United States Patent [19]
Hershey et al.

[11] Patent Number: 5,268,526
[45] Date of Patent: Dec. 7, 1993

[54] OVEREXPRESSION OF PHYTOCHROME IN TRANSGENIC PLANTS

[75] Inventors: Howard P. Hershey, West Chester, Pa.; Janis M. Keller, Wilmington, Del.

[73] Assignee: E. I. Du Pont de Nemours and Company, Wilmington, Del.

[21] Appl. No.: 284,422

[22] Filed: Dec. 14, 1988

Related U.S. Application Data

[63] Continuation-in-part of Ser. No. 226,344, Jul. 29, 1988, abandoned.

[51] Int. Cl.$^5$ .................. A01H 4/00; C12N 15/29
[52] U.S. Cl. ..................... 800/205; 800/255; 800/DIG. 9; 435/320.1; 935/35; 935/67
[58] Field of Search .............. 800/1, 200, 205, 250, 800/255, DIG. 9; 435/68, 172.1, 172.3, 320.1, 69.1; 935/9, 10, 30, 35, 47, 64, 67; 47/58

[56] References Cited
PUBLICATIONS

Potrykus (Jun. 1990) Bio/Technology 8:535-542.
Van der Krol et al., The Plant Cell, 2, 291-299 (1990).
Napoli et al., The Plant Cell, 2, 279-289 (1990).
Gardner & Gorton, Plant Physiol., 77, 540-543 (1985).
Gardner et al., Plant Physiol., 87, 8-10 (1988).
Keller et al., EMBO Jrl, 8, 1005-1012 (1989).
Gordon-Kamm et al., The Plant Cell, 2, 603-618 (1990).
Fromm et al., Bio/Technology, 8, 833-839 (1990).
Vierstra et al., Planta, 160:521-528 (1984).
Moses et al., Sci. Amer. 258(4):88-93 (1988).
Hershey et al., Gene 61:339-348 (1987).

Nagy et al., Trends in Genetics, 4:37-42 (1988).
Jordan et al., 1986 BCPC Mono No. 34 Biotechnology and Crop Improvement and Protection, pp. 49-59 (1986).
Koorneeff, et al., J. Plant Physid, 120:153-165 (1985).
Lissemore et al., Plant Molecular Biology, 8:485-496 (1987).
Keith et al., EMBO J., 5:2419-2425 (1986).
Jones et al., Biochemistry, 25:2987-2995 (1986).
Wong et al., J. Biol. Chem., 261:12089-12097 (1986).
Sharrock et al., Gene, 47:287-295 (1986).
Hershey et al., Nucleic Acid Research, 13:8543-8559 (1985).
Gelvin (1987) Plant Molecular Biology 8:355-359.
Armond, et al. (1976) Arch Biochem Biophys 175:54-63.
Noggle, et al. *Introductory Plant Physiology*, Prentice-Hall, Inc., Englewood Cliffs, N.J., U.S.A. 1976, p. 160.
Vasil (1988) Biotechnology 6:397-402.
Masoner, et al. (1975) Control of Chlorophyll ... Planta (Berl.) 126:111-117.

*Primary Examiner*—Che S. Chereskin

[57] ABSTRACT

The preparation of an uninterrupted coding sequence for phytochrome polypeptide, and its incorporation in a recombinant DNA construct containing a constitutive promoter and/or enhancer to transform plants to cause overexpression of phytochrome is described. Methods for preparing such phytochrome coding sequences by deleting the introns from genes derived from monocotyledonous plants are also described. The transgenic plants obtained using such recombinant DNA constructs exhibit a variety of useful agronomic traits.

19 Claims, 12 Drawing Sheets

COMPARISON OF PHYTOCHROME-OVEREXPRESSING PLANT, 9A, WITH NORMAL PLANT, 7A

Immunoblot of Proteins from Transgenic Plants

Lanes 1 and 10: purified Avena phytochrome

Lanes 2 and 3: etiolated seedling extracts
  Lane 2: Wild type
  Lane 3: 9A

Lanes 4 to 9: light grown shoots
  Lanes 4, 6, and 8: Harvested in light
  Lanes 5, 7, and 9: Harvested after 4 days
                     dark adaptation
  Lanes 4 and 5: 9A
  Lanes 6 and 7: 7A
  Lanes 8 and 9: 54A

OVEREXPRESSION OF PHYTOCHROME IN TRANSGENIC PLANTS

RELATED APPLICATION

The file of this patent contains at least one photograph executed in color. Copies of this patent with the color photograph will be provided by the Patent and Trademark Office upon request and payment of the necessary fee.

FIELD OF THE INVENTION

This invention relates to the preparation of uninterrupted coding sequences for phytochrome polypeptide(s), to recombinant DNA constructs used to introduce and overexpress such coding sequences in plants, and to transgenic plants and their seeds which overexpress phytochrome.

BACKGROUND OF THE INVENTION

Plants perceive light in the environment using a number of photoreceptor systems. Phytochrome is the best characterized of these photoreceptors, having been shown to play a critical role in regulating growth and development throughout the life cycle of the plant. It has been shown to be functionally involved in the control of a wide range of biological and developmental functions in plants, including such processes as de-etiolation of germinating seedlings, regulation of the synthesis of a host of plastid proteins such as those of the photosynthetic apparatus, control of shade tolerance, and regulation of the timing of flowering and fruit production [for review, see Shropshire, W., Jr., and Mohr, H. (eds.) "Photomorphorphogenesis", Encyclopedia of Plant Physiology, New Series, Vols. 16A and 16B. Springer verlag; Heidelberg/Berlin 1983]. The phytochrome molecule is now believed to be a homodimer of subunits, each known to consist of a linear tetrapyrrole chromophore covalently attached to a polypeptide backbone via a thioether linkage. The size of the polypeptide portion of the photoreceptor varies from 120-127 kilodaltons among p)ant species [Vierstra et al., Planta. 160: 521-528 (1984)]. Phytochrome exists in plants in two spectrally distinct forms; the Pr form that absorbs maximally in the red ($\lambda max=666$ nm) region of the spectrum and the Pfr form that absorbs maximally in the far-red ($\lambda max=730$ nm) region of the spectrum. The two forms are reversibly interconvertible by light; Pr is converted to Pfr by absorbing red light and Pfr is converted to Pr by absorbing far-red light. In vivo, photoconversion of Pr to Pfr by red light induces a vast array of morphogenic responses whereas reconversion of Pfr back to Pr by far-red light cancels the induction of these responses. It is this property of indefinitely repeatable photointerconvertibility that allows phytochrome to function essentially as a reversible regulatory switch, with Pr and Pfr considered to be the biologically inactive and active forms of the molecule, respectively. For a general discussion of the photoconversion process, see Moses and Chua [Moses, P. B. and Chua, N. H., Sci. Amer., 258(4):88-93 (1988)].

Although the pathway from light perception by the photoreceptor to changes in the transcription pattern of nuclear genes remains unknown, the function of phytochrome is well defined in terms of its regulation of a vast number of biological processes. Consequently, it may be that altering phytochrome levels in light-grown plants will provide a unique opportunity to noninvasively influence the complex developmental systems that regulate plant development. Further, since phytochrome plays such an important regulatory role throughout the life cycle of plants, modification of steady state phytochrome concentrations in the cells of light-grown plants may result in the creation of a number of desirable growth and developmental traits that could have potential agronomic benefit. These benefits may be in the form of genetically engineered plants with altered phenotypes such that these new phenotypes provide the plants with advantages in the field compared with their normal counterparts, thus giving rise to new plant varieties possessing improved agronomic value.

In addition, the phytochrome system is known to interact in a yet unknown way with the processes that regulate phytohormone balances in plant tissues. Modification of steady-state phytochrome levels in transgenic plants may change the balances between the various endogenous phytohormones that govern both plant morphology and development. Alterations in the steady state phytochrome levels in the tissues of light-grown plants may have dramatic effects on the development and morphology of modified plants through disruption of normal phytohormone balances, and thereby potentially give rise to plants with new traits that have agronomic value.

The genetic modification of plants to create new and useful phenotypes by altering phytochrome levels in light-grown plants through modification of plant growth and morphology is a novel concept. Hershey et al. [Hershey, H. P., Barker, R. F., Idler, K. B., Murray, M. G., and Quail, P. H., Gene 61: 339-348, (1987)] have reported the first elucidation of the sequence and organization of a phytochrome gene from a plant. The nucleotide sequence of the gene is presented along with its intron/exon organization determined from a comparison of the gene sequence with sequences derived from the corresponding cDNA clones. In addition, data is given showing the transcription start site of the gene. Sequence elements in the 5' flanking region of the phytochrome gene that may participate in its light-regulation are suggested based upon the homology of these elements with other light-regulated genes. The authors discuss the possibility of expressing phytochrome with its native promoter in a transgenic system as a method to study the role of the proposed promoter elements in the light-regulation of phytochrome gene transcription. There is no disclosure of the value or impact of either the expression or the overexpression of phytochrome on the phenotype of transformed plants.

Nagy et al. [Nagy, F., Kay, S. A., and Chua, N. H., Trends in Genetics. 4: 37-42 (1988)] review the state of phytochrome research with particular emphasis on elucidation of the signal transduction pathway that leads from the red-light induced photoconversion of Pr to Pfr through to the changes in the expression of genes regulated by phytochrome. As background for the discussion on signal transduction, the authors discuss properties of the photoreceptor, its protein structure, its localization in the plant and within the cell, its different forms, and the status of efforts to clone phytochrome coding sequences. The nature of the transcriptional regulation of phytochrome-controlled genes is discussed with emphasis on DNA sequences and transacting proteins which participate in this regulation.

Models for gene regulation and for signal transduction are proposed.

Nagy et al. (cited above) discuss future directions to be taken in phytochrome research with particular emphasis on elucidation of the signal transduction pathway. The testing of phytochrome genes which have been subjected to site directed mutagenesis in transgenic plants is suggested as a way to better understand structure/function relationships between phytochrome protein structure and altered gene expression. In this context, the authors propose overproduction of phytochrome and/or expression of the photoreceptor in inappropriate cell types as a tool to study how these changes in expression affect other phytochrome-controlled genes. They also propose the creation of dominant mutations in the phytochrome protein in order to study the signal transduction pathway by altering the functional structure of the photoreceptor. The authors concentrate their discussion and speculations on regulation of gene expression by the photoreceptor rather than on what affect, if any, expression of phytochrome would have either on gene expression or on whole plant responses in transgenic plants. In addition, no discussion of potential agronomic benefit that might result from phytochrome overexpression in whole plants appears in the article. Finally, no reports of attempts to express phytochrome in transgenic plants, either on its native promoter or by fusing a phytochrome coding sequence to a highly active constitutive promoter are disclosed in the Nagy et al. article (cited above).

Another recent review discusses the current understanding of light regulation of nuclear and chloroplast gene expression by phytochrome and UV light photoreceptors. [Jordan, B. Thomas, and Partis, M.D., in 1986 BCPC Mono No. 34 Biotechnology and Crop Improvement and Protection. Pp. 49-59, (1986)]. Suggestions are made for methods by which light-regulated genes can be manipulated to improve crop productivity. These include 1) mutational alteration of the RUBP carboxylase molecule and photoinactivation of other enzymes involved in photorespiration; 2) genetic engineering of the thylakoid membrane proteins to confer herbicide resistance and increase their abundance under low light conditions; 3) the use of controlling (promoter) sequences from light-regulated genes to control genes which are not normally light-regulated; and 4) the manipulation of the photoperiodic regulation of flowering and seed production to give more control of these processes. No specific approach to manipulating photoperiod is given and no mention is made of the possibility of genetically engineering any known plant photoreceptor to modify crop productivity.

The only known reports that discuss plants with changes in their phytochrome levels relate to mutants of tomato and arabidopsis that appear to have reduced levels of spectrally detectable phytochrome as compared to wild type plants. The mutants have been reported to display some characteristics that are somewhat similar to those seen in etiolated plants, i.e. they have more elongated hypocotyls, are more yellowish than their normal healthy green, counterparts, and appear to display some increased apical dominance [Koorneeff, M., Cone, J. W., Dekens, R. G., O'Herne-Robers, E. G., Sproit, C., J. P. and Kendricle, R. E., *J. Plant Physiol.* 120:153-165 (1985)]. No data relating to the effect of the mutation on yield or any other trait of potential agronomic value was presented, and only mutational reduction in the level of the Photoreceptor was considered.

To date, there is only one report of the isolation of a DNA fragment that contains an uninterrupted coding sequence for a complete phytochrome polypeptide [Lissemore, J. L., Colbert, J. T., Quail, P. H., *Plant Molecular Biology,* 8: 485-496 (1987)]. This article discloses the isolation of a full length cDNA clone for phytochrome from Curcurbita pepo (zucchini). However, unlike phytochrome gene expression in Avena (oats), the expression of the endogenous Curcurbita phytochrome gene is under weak, if any, phytochrome control since it displayed almost no response to Pr/Pfr photoconversion. Since the investigators did not test the responsiveness in zucchini of other genes known to be under phytochrome control in other plant species, it remains unknown if the lack of responsiveness of the zucchini phytochrome genes are due simply to a difference in the light-responsiveness of the gene or if there is some fundamental difference in regulatory function between Curcurbita and Avena phytochromes at the level of nuclear gene expression. In the absence of any further data, it seems prudent that attempts to overexpress phytochrome in transgenic plants should be made with an Avena type coding sequence since it encodes a polypeptide that is known to exert strong regulatory influence over nuclear gene expression in its native species.

Various DNA fragments containing partial Avena coding regions are available which can be combined to provide the necessary coding information to synthesize a complete phytochrome polypeptide. However, while Avena genomic clones can be combined to make a single DNA fragment encoding a complete photoreceptor molecule, the coding region would be dispersed among a number of exons as all known Avena genes contain introns. This makes existing genomic DNA fragments poor starting materials for creation of a coding region that is generally useful for expression in any transgenic plant since there is recent evidence that the introns of genes from monocotyledonous plants (of which Avena is an example) are processed poorly in dicotyledonous species. [Keith, B., and Chua, N. H., *EMBO J.,* 5:2419-2425 (1986)]. It is, therefore, necessary to produce an uninterrupted Avena phytochrome coding sequence for expression in transgenic plants since no clones containing a generally useful protein coding region are available.

Since it is well documented that light-induced differences in the conformational structures of Pr and Pfr are fundamentally involved in the mechanism of action of the photoreceptor, any changes in amino acid composition of phytochrome may negatively affect the biological efficacy of the altered protein. While it is known that the protein domains that are involved in dimerization of the subunits of phytochrome are found in the C-terminal 30 kilodaltons of the protein [Vierstra et al., 1984, as described above, Jones and Quail, *Biochemistry,* 25:2987-2995 (1986)] and the domains responsible for Pr/Pfr photoconversion are in the N-terminal 70 kilodaltons [Vierstra et al., 1984, as above, Wong et al., *J. Biol. Chem.,* 261:12089-12097 (1986)] the precise amino acids involved in these functions as well as those involved in adoption and maintenance of the Pr and Pfr secondary and higher order structures of the dimer have yet to be elucidated. Therefore, since the new phytochrome polypeptide used in this work differs from the type 3 phytochrome at 5 amino acids and differs from the type 4 phytochrome at 20 amino acids, it was unknown if the protein would be active since any single amino acid change or combination of changes could adversely affect the three dimensional structure of the protein and thus its biological activity. Indeed, it was even unknown if a monocotyledonous phytochrome would function in dicotyledonous species since there is only 65% protein homology between the only known monocot (Avena) and dicot (Cucurbita) phytochrome sequences [Sharrock et al., Gene, 47:287-295 (1986)].

Despite considerable research on the phytochrome peptide, a coding region has not been isolated which has been shown to be generally functional in both monocotyledonous and dicotyledonous plants. Furthermore, transformation constructs do not exist for overexpression of phytochrome in any plant species. The agronomic benefits of overexpression of phytochrome have therefore not been achieved.

SUMMARY OF THE INVENTION

A means to produce transgenic plants which overexpress phytochrome relative to the wild type plant in the dark and the light has been discovered. Such transgenic plants possess a number of desirable agronomic traits such as reduced apical dominance, semidwarfism, increased shade tolerance, or dark green color. Specifically, by introducing a nucleic acid fragment derived from a monocotyledonous plant comprising a single uninterrupted coding sequence for a phytochrome polypeptide into a plant utilizing a recombinant DNA construct to achieve transformation and overexpression of phytochrome one obtains one or more of the above desirable agronomic traits. While both monocotyledonous and dicotyledonous plants can be utilized to obtain embodiments of the invention, preferred monocotyledonous plants include corn, oats, millet, wheat, rice, barley, sorghum amaranth, onion, asparagus and sugar cane; and preferred dicotyledonous plants include alfalfa, soybean, petunia, cotton, sugarbeet, sunflower, carrot, celery, cabbage, cucumber, pepper, canola, tomato, potato, lentil, flax, broccoli, tobacco, bean, lettuce, oilseed rape, cauliflower, spinach, brussel sprout, artichoke, pea, okra, squash, kale, collard greens, tea and coffee. Ornamental plants also represent a preferred class of the invention. Seed obtained by growing the above transgenic plants represent the preferred means to capture and transfer the beneficial agronomic traits produced through overexpression of phytochrome.

Another aspect of the invention involves a nucleic acid fragment derived from a monocotyledonous plant comprising a single uninterrupted coding sequence for a phytochrome polypeptide, said nucleic acid fragment capable of being incorporated into a recombinant DNA construct used to transform a plant to achieve overexpression of phytochrome. Such coding sequences from monocotyledonous plants are prepared by deletion of the introns, and may be assembled from components derived from different clones in a genomic library and/or a cDNA library. Preferred coding sequences are derived from Avena following deletion of the introns.

Another embodiment of this invention involves a recombinant DNA construct capable of transforming a plant comprising a single uninterrupted coding sequence for a phytochrome polypeptide made functionally operational by linkage at the 5' end to a nucleic acid promoter fragment and at the 3' end to a regulatory sequence containing a polyadenylation signal(s) such that upon transformation said plant overexpresses phytochrome relative to the wild type plant in the dark and in the light. Preferred recombinant DNA constructs involve nucleic acid promoter fragments derived from the genome of a virus or from Agrobacterium. More preferred nucleic acid promoter fragments are derived from the 35S or 19S constituents of the cauliflower mosaic virus, or from the opine synthase genes of Agrobacterium. Optionally, the nucleic acid promoter fragment may contain an enhancer to further stimulate transcription and expression, with preferred enhancers obtained from a virus or Agrobacterium. More preferred enhancers are obtained from the 35S constituent of cauliflower mosaic virus or the opine synthase genes of Agrobacterium. Most preferred, by virtue of activity or ease of preparation, are recombinant DNA constructs comprising single uninterrupted coding sequences for phytochrome polypeptide derived from Avena operably linked to a nucleic acid promoter fragment obtained from the 35S constituent of cauliflower mosaic virus and a 3' polyadenylation signal sequence obtained from the Avena phytochrome gene. Incorporating the above recombinant DNA constructs into transformation vectors such that they will be mobilized with the T-DNA region of the *Agrobacterium tumefaciens* Ti plasmid into plants following infection of the plant by the bacteria provides the most preferred means to transform plant tissue.

BRIEF DESCRIPTION OF THE DRAWINGS

The file of this patent contains at least one photograph executed in color. Copies of this patent with color photograph will be provided by the Patent and Trademark Office upon request and payment of the necessary fee.

DETAILED DESCRIPTION OF THE INVENTION

The present invention provides a method to increase the steady-state level of phytochrome in the cells of genetically engineered plants to modify the growth and morphological characteristics for the improvement of their agronomic and commercial value. Phytochrome is a soluble protein found in all plants that functions in a regulatory capacity to control a wide variety of biological processes. Analysis of phytochrome from various species shows them to consist of two identical subunits each composed of a polypeptide chain with molecular masses ranging from 120–127 kilodaltons. Each subunit consists of a linear tetrapyrrole chromophore covalently attached to the protein via a thioether linkage. The presence of phytochrome in etiolated plant tissues is often determined by measurement of the photoreceptor's characteristic difference spectrum (the spectrum obtained by subtraction of the spectrum of Pfr from Pr). The presence of massive amounts of chlorophyll in green plant tissues, however, interferes with spectral measurements of the photoreceptor. The generation of both polyclonal antibodies that recognize phytochrome from a variety of plant species as well as highly specific monoclonal antibodies that recognize only Avena phytochrome has facilitated the analysis of the photoreceptor in green plants. Analyses of Avena phytochrome expression in transgenic plants is performed in this work either immunochemically or spectrally depending on the tissues being analyzed.

The invention is utilized to increase intracellular phytochrome levels in plant species of interest by introduction of a nucleic acid fragment containing a single uninterrupted coding sequence for a phytochrome polypeptide that is made operationally functional in a desired plant species by its linkage to a genetic sequence capable of increasing the level of expression of the phytochrome coding sequence and a sequence capable of providing a polyadenylation signal for proper RNA processing. When such a combination is present in a plant, the plant should display modification in a desirable manner of one or more growth and morphological characteristics, such as reduced apical dominance, semidwarfism, increased shade tolerance, and dark green color. These modifications are of great value in crop plants where wind damage of tall species causes significant yield losses, and in ornamental plants where greener, shorter, bushier plants are highly desired. Such modifications are currently sought by exposing plants to cytokinin hormone compounds which also induce numerous side effects.

Figure 1:
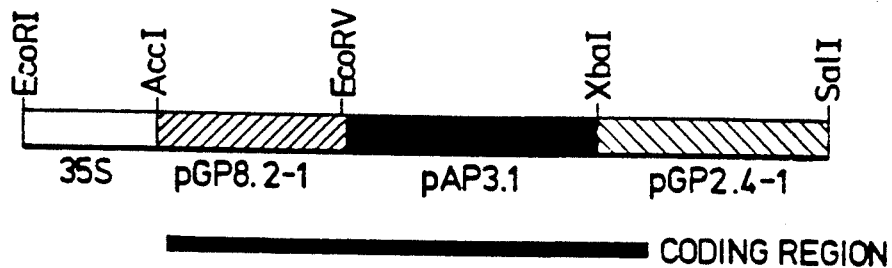
FIG. 1 is a physical map of pCV35phyt showing regions from different clones which were linked to create the recombinant DNA construct.

A recombinant DNA construction representing a chimeric phytochrome gene of the type described above was created (as shown in FIG. 1) that consists of a 1 kbp (one thousand base pairs) 35S promoter fragment from the Cauliflower Mosaic Virus 35S transcript operationally linked to a chimeric phytochrome sequence. The chimeric phytochrome sequence consists of 1438 bp of phytochrome coding sequence from the Avena type 3 (See Hershey et al., Nucleic Acid Res., 13:8543–8559 (1985), for a description of nomenclature) genomic clone, pGP8.2-2 (from the Acc I to Eco Rv sites of the plasmid), linked to 1862 bp of Avena type 3 cDNA coding sequence from clone pAP3.1 (the Eco RV to Xba I fragment from this plasmid) and terminated with 1733 bp from Avena type 4 genomic clone pGP2.4-1 (the Xba I to Eco RI fragment of pGP2.4-1) that completes the coding region and provides polyadenylation signals and any other regulatory functions that may be required at the 3' end of a plant gene. The resulting construction encodes an 1129 amino acid phytochrome polypeptide in an uninterrupted DNA sequence. The recombinant DNA construction was used to transform tobacco plants using Agrobacterium-mediated leaf disk infection. The tobacco plants that were regenerated from the transformation show expression of functional chimeric phytochrome protein and display increased steady-state levels of total phytochrome both in the light and in the dark. The tobacco transformants expressing the chimeric gene all show increased green pigmentation, increased tillering (more stems formed from the base of the plant), a marked reduction in apical dominance, and reduced internodal distance, resulting in plants with a semi-dwarf phenotype such that transformed plants have the same number of leaf nodes to inflorescence but approximately half the height of normal plants.

The creation of a phytochrome coding region with general utility is accomplished in this invention by combining portions of two independent genomic Avena phytochrome clones representing pieces from two different phytochrome genes with one Avena cDNA clone. The cDNA clone used here, designated pAP3.1 [Hershey et al., Nucleic Acids Res., 13:8543–8559 (1985)], encodes the central section of the phytochrome polypeptide, but lacks both 5' and 3' sequences that encode the N-terminal and C-terminal protein domains of the photoreceptor. A fragment from the genomic clone pGP8.2-2 (Hershey et al.,1985, as described above) that contains the 5' coding sequences from exon 2 which are missing from the cDNA clone was used to complete the N-terminal coding region of the photoreceptor and to provide a 5' untranslated leader for the coding region. The 3' coding sequence and polyadenylation sequences which are missing from pAP3.1 were derived from the genomic clone designated λGP2.4. pGP2.4-1 is the 5.5 kbp Eco RI fragment from the genomic clone pGP2.4 subcloned into the Eco RI site of pBR322 (Hershey et al. 1985, as described above). The novel protein sequence which is encoded by the resulting DNA fragment is a fusion protein consisting of portions of type 3 and type 4 phytochromes (Hershey et al. 1985) and does not exist in nature.

The invention also comprises a gene combination as described above, present either in the plant genome or as a replicating extrachromosomal element for the case where the phytochrome protein produced is any phytochrome native to the species in which it is expressed or a heterologous protein derived from the coding region of another plant species. Indeed, the phytochrome coding region may consist of any heterologous or homologous coding region that will result in production of a functional phytochrome in the desired plant.

The origin of the promoter chosen to drive the expression of the phytochrome coding region is not critical as long as it has sufficient transcriptional activity to accomplish the invention by increasing the steady-state level of phytochrome in light and dark grown plants. The promoter region used in the invention herein is derived from the 35S transcript of cauliflower mosaic virus. Promoters such as those derived from the 19S gene of the cauliflower mosaic virus, the opine synthesis genes (NOS, OCS) from various Agrobacterium strains, the promoter from the RUBP carboxylase genes, the chlorophyll A/B binding protein genes, the RUBISCO promoter of plant origin, or the promoter from any gene from any source that provides for sufficiently high levels of transcription of the phytochrome region to which it is linked are expected to accomplish the invention.

It is envisioned that the introduction of enhancers or enhancer-like elements into either the native phytochrome promoter or into other promoter constructs will also provide increased phytochrome levels by the increased transcriptional activity of a gene encoding phytochrome to accomplish the invention. This would include viral enhancers such as that found in the 35S Promoter, Odell et al. 1987 [Odell, J. T., Knowlton, S., Lin, W. and Mauvars, C. J., Plant Mol. Biol. 10:263-272 (1988)], enhancers from the octopine synthase or nopaline synthase genes, or enhancers from any other source that result in increased transcription when placed into a promoter operably linked to a phytochrome coding sequence.

The phytochrome coding sequence may or may not contain introns in order to accomplish the invention. A coding region without introns may be preferable since such a coding region avoids possible post-transcriptional processing of the phytochrome primary transcript due to potential differences in the mechanisms responsible for intron deletion among various plant species. It is expected that any phytochrome coding region that will provide for the expression of an active phytochrome in a plant regardless of the source of the coding sequence may be sufficient to accomplish the invention. This would include phytochrome coding regions from monocotyledenous plants introduced into either other monocots or dicot species and the use of dicotyledenous phytochromes in either dicots or monocots. Indeed, since phytochrome coding sequences have been so functionally conserved through evolution, it may be expected that phytochromes from algal species may also be useful in accomplishing the invention. The only requirement of the coding region used is that it can provide an active phytochrome in the desired plant species upon transformation of a plant with such a coding region operably linked to appropriate 5' and 3' regulatory sequences required for its proper expression.

Any 3' non-coding region capable of providing a polyadenylation signal and other regulatory sequences that may be required for the proper expression of the phytochrome coding region can be used to accomplish the invention. This would include the native 3' end of the homologous phytochrome gene of the plant species to be modified, the 3' end from a heterologous phytochrome gene, the 3' end from viral genes such as the 3' end of the 35S or the 19S cauliflower mosaic virus transcripts, the 3' end from the opine synthesis genes, the 3' ends of RUBISCO or CAB genes, or 3' end sequences from any source such that the sequence employed provides the necessary regulatory information within its nucleic acid sequence to result in the proper expression of the promoter/phytochrome coding region combination to which it is operably linked.

The invention can also be accomplished by a variety of other methods to obtain the desired end. In one form, the invention is based on modifying plants to produce increased levels of phytochrome by virtue of having significantly larger numbers of copies of either the wild type or a heterologous phytochrome gene in the plants. This may result in sufficient increases in phytochrome levels to accomplish the invention.

Phytochrome is known to be rapidly degraded in plants grown in the light. Another form of the invention consists of modifying the phytochrome protein itself to significantly increase the cellular half-life of the protein to obtain a higher steady state level of the photoreceptor in the light. Since phytochrome is known to be degraded via a ubiquitin mediated pathway [Shanklin et al., Proc. Natl. Acad. Sci USA., 84:359-363 (1987)], the invention may be accomplished by modification of the ubiquitin recognition sites in phytochrome to increase phytochrome levels by reducing the degradation rate of the protein in the light.

The examples of the invention given below are for phytochrome overexpression in tobacco, tomato and brassica, but since phytochrome is highly conserved functionally throughout the plant kingdom, the invention may be accomplished in a wide variety of plant species by transforming them to a phenotype of phytochrome overexpression. The species of agronomic importance which would benefit by increased photosynthetic activity especially in low light conditions, by dwarfism or by reduced apical dominance include but are not limited to rice, wheat, corn, soybean, oilseed rape, lettuce, sunflower, apple and other fruit tree varieties. It has been found with rice, for example, that varieties which are semi-dwarf, with dark green leaves, give the best yields due to increased resistance to lodging, as well as enhanced photosynthetic output during grain production [for review see McKenzie et al., in *Principle of Cultivar Development*, (W. Fehr, ed.), Vol. 2, 487-532. MacMillan: New York 1987]. The ability to induce these traits in rice varieties which are not naturally dwarfed but display other advantageous traits such as cold tolerance or pest resistance would be of great agronomic benefit. Semi-dwarfism has been found to be beneficial for yield enhancement in other important crop plants such as soybean [Fehr, W., in *Principle of Cultivar Development*, (W. Fehr, ed.), Vol. 2, 533-576. MacMillan: New York 1987], sunflower [Miller, J. F., in *Principle of Cultivar Development*, (W. Fehr, ed.), Vol. 2, 6260668. MacMillan: New York 1987], and wheat [Allan, in *Principle of Cultivar Development*, (W. Fehr, ed.), Vol. 2, 699-748. MacMillan: New York 1987]. In addition, wheat may be beneficially affected through overproduction of phytochrome by making it less sensitive to photoperiod (a phytochrome dependent trait) and thereby allowing it to mature earlier in the season. Further, the induction of a darker green phenotype through modification of plants to overexpress phytochrome may improve marketability of green vegetables such as lettuce and ornamental plants such as chrysanthamum due to improved consumer appeal. It may be that increased photosynthetic activity in plants used for animal forage, such as alfalfa and clover, will make them more valuable foodstuffs as well by increasing the deposition of biomass into seeds.

In the context of this disclosure, a number of terms shall be utilized. As used herein, the term "promoter region" refers to a sequence of DNA, usually upstream (5') to the coding sequence of a structural gene, which controls the expression of the coding region by providing the recognition for RNA polymerase and/or other factors required for transcription to start at the correct site. Promoter sequences are necessary but not always sufficient to drive the expression of a gene. A "promoter fragment" constitutes a fraction of the DNA sequence of the promoter region. An "enhancer" is a type of DNA fragment which can operate in an orientation and location independent manner to stimulate promoter activity. An enhancer may also designate a transcription stimulator sequence as described in Odell et al., *Plant Molecular Biology*, 10:263-272 (1988). "Nucleic acid" refers to a large molecule which can be single stranded or double stranded, composed of monomers (nucleotides) containing a sugar, phosphate and either a purine or pyrimidine. A "nucleic acid fragment" is a fraction of a given nucleic acid molecule, usually obtained by restriction endonuclease digestion of the larger nucleic acid molecule. In higher plants, deoxyribonucleic acid (DNA) is the genetic material while ribonucleic acid (RNA) is involved in the translation of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. As used herein, "DNA sequences for selected gene products" refers to a gene of DNA sequences that codes for a specific protein. "Regulatory sequence", as used herein, refers to a nucleotide sequence located upstream (5′), within, and/or downstream (3′) to a DNA sequence for a selected gene product whose transcription and expression is controlled by the regulatory sequence in conjunction with the protein synthetic apparatus of the cell. The term "structural gene" refers to that portion of a gene encoding a protein, polypeptide, or a portion thereof, and excluding the regulatory sequences which drive the initiation of transcription and RNA processing. A structural gene may normally be found in the cell or it may be found in a cellular location wherein it is introduced, in which case it is termed a heterologous gene. A "heterologous gene" may be derived in whole or in part from any source known to the art, including a bacterial genome or episome, eukaryotic nuclear or plasmid DNA, cDNA, or chemically synthesized DNA. The structural gene may constitute an "uninterrupted coding sequence", i.e., not requiring intron excision from the messenger RNA prior to its translation to a protein molecule, or it may include one or more introns bounded by appropriate splice junctions. An "intron" is a sequence of RNA which occurs in the initial transcript synthesized from the DNA, but is removed through cleavage and religation of the RNA within the cell to create the mature messenger RNA, which can then be translated into the protein. The structural gene may be a composite of segments derived from different sources, naturally occurring or synthetic. If a structural gene is made up of a composite of segments derived from different sources, it is frequently referred to as a "chimeric gene". 3′ untranslated sequence refers to that portion of a gene comprising a DNA segment containing a polyadenylation signal and any other regulatory signals capable of effecting mRNA processing at the promoter distal end of the coding sequence. The polyadenylation signal is usually characterized by affecting the addition of polyadenylic acid tracts to the 3′ end of the mRNA precursor. Polyadenylation signals are commonly recognized by the presence of homology to the canonical form 5′-AATAAA-3′, although variations are not uncommon. The term "recombinant DNA construct" refers to a plasmid, virus, autonomously replication sequence, phage or nucleotide sequence, linear or circular of a single- or double-stranded DNA or RNA, derived from any source, in which a number of nucleotide sequences have been joined or recombined into a unique construction which is capable of introducing a promoter fragment and DNA sequence for a selected gene product along with appropriate 3′ untranslated sequence into a plant cell.

As used herein, "monocotyledonous plant" refers to a plant whose seeds have only one cotyledon, or organ of the embryo which stores and absorbs food. A "dicotyledenous plant" refers to a plant whose seeds have two cotyledons. A "protoplast" refers to a plant cell without a cell wall or extracellular matrix. "Reduced apical dominance" refers to a condition in plants in which the main apical meristem has less influence over the axilary buds so that increased leafing and branching occur from the meristem of the plant. "Semi-dwarfism" refers to plants which are smaller by about one half than normal plants of the same species but otherwise have normal structure (i.e., same number of stem nodes to inflorescence, same number of flowers).

As used herein, "transformation" means processes by which cell/tissue/plant acquire properties encoded on a nucleic acid molecule that has been transferred to the cell/tissue/plant. "Transferring" refers to methods to transfer DNA into cells including microinjection, or permeabilizing the cell membrane with various physical (e.g., electroporation) or chemical (e.g., polyethylene glycol, PEG) treatments. Plants acquiring new traits as a result of transformation with a nucleic acid are referred to as "transgenic plants". As used herein, "exposing" a protoplast or a plant to a chemical substance refers to treating, incubating, contacting said protoplast or plant with the substance. The term, "operably linked" refers to the chemical fusion of two fragments of DNA in a proper orientation and reading frame to be transcribed into functional RNA. As used herein, the term "homologous to" refers to proteins having similar amino acid sequences. The term "expression" as used herein is intended to mean the translation to gene product from a gene coding for the sequence of the gene product. In the expression, a DNA chain coding for the sequence of gene product is first transcribed to a complementary RNA which is called a messenger RNA and, then, the thus transcribed messenger RNA is translated into the above-mentioned gene product. Expression, which is constitutive and further enhanced by an externally controlled promoter fragment thereby producing multiple copies of messenger RNA and large quantities of the selected gene product, is referred to as "overexpression". The "translation start codon" refers to a unit of three nucleotides (codon) in a nucleic acid that specifies the initiation of the protein coding sequence.

The techniques of DNA recombination used throughout this invention are known to those skilled in the art and are generally described in Maniatis et al., Molecular Cloning: A Laboratory Manual, Cold Spring Harbor (1983).

Enzymatic Treatments of DNA

1. Restriction Enzyme Digestions

The restriction enzyme digestion buffers and digestion conditions used are those supplied by the manufacturer of each particular enzyme. When recommended by the manufacturer, dithiothreitol (DTT) is added from a separate sterile stock solution to the recommended concentration. Enzyme is added to give 5-10 units per microgram of DNA and the reaction mixture is adjusted to the appropriate final volume with water (usually 10–20 μl). The restriction enzyme reaction mixtures used routinely contained 0.7–2.0 ug plasmid DNA. The reaction components are mixed and then incubated at the appropriate temperature for 1 to 3 hours. Digestion of DNA with multiple enzymes is done concomitantly when the optimal salt and temperature conditions of the separate enzymes are similar. When these conditions are sufficiently different, digestions are done sequentially beginning with the enzyme requiring the lowest salt concentration. Subsequent reactions are supplemented to the appropriate buffer conditions for the enzyme used.

2. Blunt-ending Reactions

It is necessary, on occasion, to render the ends of a restriction fragment blunt prior to ligation. The blunt-ending reaction utilizes the Klenow fragment of E. coli DNA polymerase I. The reaction mixture is 1 unit of Klenow fragment per μg of DNA, 50 mM of each of the four deoxynucleoside triphosphates (dNTPs) in 50 mM Tris-HCl, pH 7.5, 0–50 mM NaCl, 5–10 $MgCl_2$, 5 mM DTT and is incubated at room temperature (22° C.) for 15–30 minutes (to fill in 5′ overhangs) or for 2 hours (to remove 3′ overhangs). When convenient, the reaction is performed in the same tube in which the reaction with the restriction enzyme(s) took place. In those cases, the salt concentration is adjusted to a final concentration of less than 50 mM. When secondary restriction digestion(s) are to be performed, the Klenow fragment is inactivated by heating it to 65°–70° C. for 10–15 minutes prior to adding the second restriction enzyme.

3. Phosphatase Reactions

During ligation, DNA ligase will catalyze the formation of a phosphodiester bond between adjacent nucleotides only if one nucleotide contains a 5′-phosphate group and the other a 3′-hydroxyl group. Recircularization of plasmid DNA can therefore be minimized by removing the 5′ phosphates from both ends of the linear DNA with bacterial alkaline phosphatase or calf intestinal phosphatase. As a result, neither strand of the duplex can form a phosphodiester bond. However, a foreign DNA segment with 5′-terminal phosphates can be ligated efficiently to the dephosphorylated plasmid DNA to give an open circular molecule containing two nicks. Circular DNA (even nicked circular DNA) transforms much more efficiently than linear plasmid DNA. Consequently, most of the transformants will contain recombinant plasmids.

Phosphatase treatment is performed after restriction endonuclease digests or Klenow treatment by making the DNA containing solution 0.1M in Tris-HCl pH 8.4 and incubation of the solution with 0.5 units of calf intestinal alkaline phosphatase (CIP) per microgram of DNA (Boehringer Mannheim Biochemicals) at 55° C. for 15 minutes. The phosphatase is inactivated by heating at 70° C. for 15 minutes, followed by seguential extractions of the DNA solution with equal volumes of phenol (phenol as used is saturated with 0.1M Tris-HCl, pH 8.0 prior to use), phenol:chloroform (1:1) and chloroform. The DNA precipitated to concentrate it by addition of sodium acetate to a final concentration of 0.3M followed by addition of two volumes of ethanol.

4. Ligation

For ligation of DNA fragments, T4 DNA ligase (Pharmacia, Piscataway, N.J.) and ligase buffer (50 mM Tris-HCl, pH 7.5, 10 mM $MgCl_2$, 1.0 mM DTT, and 1.0 mM ATP) are used. When blunt-ended DNAs are ligated, polyethylene glycol 8000 (PEG 8000) is added to the ligation mixture to a final concentration of 5% (w/v). Two to five units of enzyme are added per microgram of DNA. The reaction mixtures are incubated at 16° C. overnight.

Gel Electrophoresis of DNA

For polyacrylamide gel electrophoresis of DNA, the Tris-Borate-EDTA (TBE) buffer (Bethesda Research Laboratories, Gaithersburg, Md. 20877) which consists of 89 mM Tris and 89 mM borate (pH 8.3), 2.5 mM $Na_2EDTA$ is used. The gels used consisted of 4.5% acrylamide and 0.15% bis-acrylamide dissolved in 100 ml 1X TBE containing 25% glycerol. To this solution, 0.05 gm ammonium persulfate and 35 ul of N,N,N′,N′-Tetra-methylethylenediamine (TEMED) is added and the solution is poured into a gel mold. Two mm comb and spacers are commonly used and approximately 10 to 15 μg of DNA is loaded per well. Electrophoresis is carried out at 150–250 volts in 1 X TBE. After electrophoresis, the gel is stained in an aqueous solution of ethidium bromide (1 μg/ml) and the DNA is visualized on an ultraviolet transilluminator. The gel is photographed using a Polaroid camera and Polaroid 667 film (Polaroid Tech. Photo, Cambridge, Mass. 02139).

DNA is recovered from polyacrylamide gels as follows: The desired band, visualized by ethidium bromide (EtBr) staining, is cut from the gel, placed in an Eppendorf tube and minced with a spatula. An equal volume of gel elution buffer (0.5M ammonium acetate, 14 mM Mg acetate, 1 mM EDTA, and 0.1% SDS solution) is added and the tube is incubated at 37° C. overnight with vigorous shaking. The following day, the liquid is drained from the acrylamide by passing it through a 1 ml pipetting tip containing a glass wool plug. The acrylamide is rinsed with a second volume of gel elution buffer, and the liquid is forced from the tip using a 1 ml Pipetman pipetter. The DNA is then precipitated by addition of 2 volumes of ethanol and incubation in dry ice-ethanol. The DNA is collected by centrifugation of the sample in a microfuge, as above, for 15 minutes at 4° C. The pellet is then rinsed with 70% ethanol, dried under vacuum and resuspended in the buffer of choice depending on the nature of the next manipulation.

Agarose gel electrophoresis of DNA is performed in 0.7 to 1.2% agarose gels (depending the size of the DNA fragments being analyzed) using the buffer described above for polyacrylamide gels. Electrophoresis is conducted at a voltage of 50 to 150 volts depending on the amount of DNA per lane and the desired timing of the run. After electrophoresis, the gel is stained with 1 μg/ml of EtBr and the DNA is visualized on an ultraviolet transilluminator and photographed as described above.

DNA is recovered from agarose gels using low temperature gelling agarose (Sea Plaque Agarose from FMC Corporation, Marine Colloids Division, Rockland, Me. 04841). The electrophoresis procedure is stated above. After visualization of the DNA of interest, the band is cut out and placed into an Eppendorf tube. The tube is than frozen at −80° C. for 30 minutes and than thawed. The agarose is then crushed with a spatula and the sample is centrifuged in a microfuge for 10 minutes. The supernatant is removed from the tube without disturbing the agarose pellet at the bottom of the tube. The sample is precipitated with the addition of 1/10 volume of 3M sodium acetate and 2 volumes of ethanol followed by a 15-30 minute incubation at −80° C. The DNA is recovered by centrifugation in a microfuge for 15 minutes at 4° C. The DNA pellet is than washed with 70% ethanol, dried under vacuum and resuspend in TE buffer.

Transformation of Bacterial Cells

Transformation of *E. coli* with plasmid DNA was performed with Bethesda Research Laboratories frozen competent cells. The protocol followed is supplied with the cells.

The competent cells are removed from storage in a −80° C. freezer and thawed on ice. The required number of 17×100 mm polypropylene tubes (Falcon 2059) are placed on ice for pre-chilling. The cells are gently mixed and then 100 μl aliquots are placed into each tube. The ligation mixtures are diluted 5 fold with water before addition to the cells. Two μl of the diluted ligation mixture is added to the cells and this is incubated on ice for 30 minutes. The cells are then heat shocked for 45 seconds in a 42° C. water bath without shaking. The cells are returned to the ice for 2 minutes before addition of 0.9 ml of S.O.C. medium is added. S.O.C. medium is composed of 2% Bacto tryptone, 0.5% Yeast Extract, 10 mM NaCl, 2.5 mM KCl, 20 mM $MgCl_2$, $MgSO_4$ (10 mM each) and 20 mM glucose. The cells are then shaken at 225 RPM at 37° C. for 1 hour. After this growth period, the cells are plated on LB plates which contain the appropriate antibiotic for selection of the transformed plasmid. Usually several different volumes of cells are added per plate (i.e., 1.5, 15 and 150 ul) and the plates are then incubated at 37° C. overnight for the colonies to grow-up.

When it is necessary to cleave DNA at a restriction site where the endonuclease is sensitive to dam methylation, the plasmid containing the desired DNA fragment is grown in a dam- strain of *E. coli*. Strain NS2626 is used in this work, but any commonly available dam- strain of *E. coli* can be used. Competent dam- cells are obtained by inoculating 50 ml of LB broth with 100 ul of an overnight culture, incubating them at 37° C. with shaking until the $O.D._{650}$ is 0.250, and then chilling the cells to 0° C. on ice. The bacteria are harvested by centrifuging at 1500 × g for 10 min., followed by resuspension in 25 ml of 100 mM $CaCl_2$ and incubation on ice for 30 min. The bacteria are recentrifuged (as above) and resuspended in 1 ml of 100 mM $CaCl_2$. After 4 hours on ice, 200 ul of competent cells are removed, 1 μg of plasmid DNA is added, and the cells are incubated on ice for 30 minutes. The cells are then heat shocked for 2 minutes in a 42° C. water bath without shaking. The cells are returned to the ice for 2 minutes before addition of 1 ml of S.O.C. medium. The transformation proceeds as described above.

Plasmid Isolation and Purification

1. Large Scale Preparation

A 25 ml overnight culture (or exponentially growing culture) of the bacteria containing the desired plasmid is prepared. Then dilute 2 ml of the overnight into 1 liter of M9CA or L broth (as described in Molecular Cloning: A Laboratory Manual, Maniatis T. et al., Cold Spring Harbor Laboratory, Cold Spring Harbor, N.Y.) and incubate for 16 hours [overnight] at 37° C. with vigorous shaking. Collect the bacteria by centrifugation at 4000 × g for 5 min at 4° C. Drain the pellets well and resuspend them in a total volume of 36 ml of GTE buffer [50 mM glucose, 25 mM Tris-HCl, pH 8 and 10 mM EDTA]. Add 4 ml of 40 mg/ml lysozyme in GTE to the suspension and incubate the mixture at room temperature for ten minutes. Cool the cell suspension on ice and add 80 ml of freshly made 0.2N NaOH and 1% SDS with gentle swirling. Incubate the mixture on ice for 10 min. Add 40 ml of 3M potassium acetate in 2M acetic acid and mix well. The mixture is then incubated on ice for 15 minutes. Remove the precipitate by centrifugation at 24,000 ×g [12 K RPM] for 15 minutes and filter the supernatant through 4-5 layers of cheesecloth. Precipitate the nucleic acids by addition of 0.6 volumes of isopropanol. Collect the resulting precipitate by centrifugation at 12,000 rpm for 10 minutes at 15° C. Wash the pellet with 70% ethanol (in TE buffer) and re-pellet the DNA as before. Dissolve the nucleic acid pellet in 10 ml of TE, pH 8. After the DNA has dissolved, add 1.0 g of CsCl for each ml of dissolved DNA. Add 0.32 ml of ethidium bromide (EtBr) to the DNA solution from a 10 mg/ml stock solution (final concentration of 600 μg/ml). Band the plasmid DNA by centrifugation at 65,000 rpm for at least 15 hr. in a Beckman 70.1 Ti rotor or equivalent at 20° C. The gradient generally contains three bands. The lowest band absorbs no ethidium bromide, while the two upper bands do absorb the dye. The less dense top band which corresponds to chromosomal DNA often can barely be seen. Remove the plasmid band, which is the lower of the two absorbing bands from the gradient by puncturing the side of the tube below the band with a 20 gauge needle and drawing the DNA out of the tube. Remove the EtBr by repeated extraction of the DNA with 80% isopropanol saturated with NaCl (made by adding 10 ml of 50 mM Tris-HCl, pH 8.0, 1 mM EDTA and 10 ml of 5M NaCl to 80 ml of 2-propanol). Dilute the extracted plasmid with two volumes of TE, pH 8.0 and precipitate the DNA with 2 volumes of ethanol at −20° C. for at least one hour. Recover the DNA by centrifugation at 10,000 × g for 30 minutes at 4° C. Resuspend the DNA in TE buffer and re-precipitate it by addition of sodium acetate to 0.3M followed by two volumes of ethanol. Recover the DNA as above and resuspend in TE buffer and store at −20° C.

2. Small Scale Preparation

Inoculate 5 ml of medium containing the appropriate antibiotic with a single bacterial colony. Incubate at 37° C. overnight with vigorous shaking. Pour 1.5 ml of the culture into an Eppendorf tube. Centrifuge for 20 seconds in an Eppendorf centrifuge. Remove the medium by aspiration, leaving the bacterial pellet as dry as possible. Repeat in the same tube. Store the remainder of the overnight culture at 4° C. or make a stock plate of each pick on a numbered matrix to establish identity of each colony. Resuspend the pellet by vortexing in 100 ul of an ice-cold solution of GTE buffer containing 4 mg/ml lysozyme (added to the solution just before use). Incubate for 5 minutes at room temperature. The top of the tube need not be closed during this period. Add 200 μl of a freshly prepared solution of lysis buffer (0.2N NaOH and 1% SDS). Close the top of the tube and mix the contents by inverting the tube rapidly two or three times. Do not vortex. Store the tube on ice for 5 minutes. Add 150 μl of an ice-cold solution of potassium acetate (pH 4.8) made up as follows: to 60 ml of 5M potassium acetate, add 11.5 ml of glacial acetic acid and 28.5 ml of $H_2O$. The resulting solution is 3M with respect to potassium and 5M with respect to acetate. Close the cap of the tube and mix by inverting the tube sharply several times. Store on ice for 5 minutes. Centrifuge for 5 minutes in an Eppendorf centrifuge at 4° C. Transfer the supernatant to a fresh tube and add an equal volume of phenol/chloroform. Mix by vortexing. After centrifuging for 2 minutes in an Eppendorf centrifuge, transfer the supernatant to a fresh tube. Add two volumes of ethanol at room temperature. Mix by inverting. Stand at room temperature for 2 minutes. Centrifuge for 5 minutes in an Eppendorf centrifuge at room temperature. Remove the supernatant and stand the tube in an inverted position on a paper towel to allow all of the fluid to drain away. Add 250 ul of 70% ethanol. Mix briefly and then recentrifuge Again remove all of the supernatant Dry the pellet briefly in a vacuum desiccator Add 50 ul of TE (PH 8.0) containing DNase-free pancreatic RNase (20 µg/ml) and vortex briefly. Remove 2 ul of the solution to a new Eppendorf tube. Add 6 ul of water, 1 ul of appropriate 10 X restriction buffer, and 1 ul of the desired restriction enzyme(s) Incubate for 1-2 hr at the appropriate temperature (37° C.) Store the remainder of the preparation at −20° C. Analyze the DNA fragments in the restriction digest by gel electrophoresis.

Triparental Mating

In order to introduce DNA constructions of interest into plants to test their activity, the constructions are mobilized from *E. coli* strain HB101 into *Agrobacterium tumefaciens*, strain GV3850. *E. coli* strain HB101 containing the plasmid pRK2013 is used as a helper for plasmid mobilization in a triparental mating. Each strain of bacteria, HB101 (containing the construct), HB101 (pRK2013), and GV3850 is separately grown overnight in 5 ml of Luria Bertani (LB) broth in the presence of the appropriate selective antibiotic. The cells from the cultures are harvested by centrifugation at 4000X g for 10 minutes at 22° C. and then resuspended in 5 ml LB broth. The mating is performed by mixing 100 ul of each of the three cultures in a 1.5 ml Eppendorf centrifuge tube and pipetting the entire mixture onto sterile nitrocellulose discs (Millipore HA type filters). Each nitrocellulose disk is placed on 6-8 sterile Whatman #1 filter paper disks to remove excess liquid from the culture and thereby concentrate the bacteria in the mixture. The nitrocellulose disks is then placed onto LB agar in a 100 mm petri dish and incubated for approximately 16 hours at 30° C. Following the incubation, the bacteria are washed from the nitrocellulose discs into a sterile 4 ml polypropylene culture tube using 1 ml of 10 mM MgSO$_4$. The bacteria are serially diluted and various dilutions are plated onto LB agar plates containing 100 ug/ml each of rifampacin, spectinomycin, and streptomycin (or other appropriate antibiotic combination). After a 3 day incubation at 30° C. resistant colonies are selected and the presence of the desired insert DNA is confirmed by Southern blot analysis of Ti plasmids prepared from individual colonies using the small scale plasmid isolation described above.

Transformation of plants

Constructions are mobilized into the plant genome via *Agrobacterium tumefaciens* infection of tobacco leaf disks. Standard aseptic techniques for the manipulation of sterile media and axenic plant/bacterial cultures are followed, including the use of a laminar flow hood for all transfers. Potted tobacco plants for leaf disk infections are grown in a growth chamber maintained for a 12 hour, 24° C. day, 12 hour, 20° C. night cycle, with approximately 80% relative humidity, under mixed cool white flourescent and incandescent lights. Tobacco leaf disk infections are carried out essentially by the method of Horsch et al. (Horsch, R. B., Fry, J. E., Hoffman, N. L., Eichholtz, D., Rogers, S. G., and Fraley, R. T. (1985) Science, 227, 1229-1231).

Young leaves, not fully expanded and approximately 4-6 inches in length are harvested with a scalpel from approximately 4-6 week old tobacco plants. The leaves are surface sterilized for 30 minutes by submerging them in approximately 500 ml of a 10% Chlorox, 0.1% SDS solution and then rinsing them 3 times with sterile deionized water. Leaf disks, 6 mm in diameter are prepared from whole leaves using a sterile paper punch.

Leaf disks are inoculated by submerging them for several minutes in 20 ml of a 1:10 dilution of an overnight LB broth culture of Agrobacteria carrying the plasmid of interest. After inoculation, the leaf disks are placed in petri dishes containing CN agar medium (1 bag MS salts (Gibco) 30 gm sucrose, 8 gm agar, 0.1 ml of 1 mg/ml NAA, and 1 ml of 1 mg/ml BAP per liter, pH 5.8). The plates are sealed with parafilm and incubated under mixed fluorescent and "Gro and Sho" plant lights (General Electric) for 2-3 days in a culture room maintained at approximately 25° C.

To rid the leaf disks of Agrobacteria and to select for the growth of transformed tobacco cells, the leaf disks are transferred to fresh CN medium containing 500 mg/L cefotaxime and 100 mg/L kanamycin. Cefotaxime is kept as a frozen 100 mg/ml stock and added aseptically (filter sterilized through a 0.45 uM filter) to the media after autoclaving. A fresh kanamycin stock (50 mg/ml) is made for each use and is filter sterilized into the autoclaved media.

Leaf disks are incubated under the growth conditions described above for 3 weeks and then transferred to fresh media of the same composition.

Approximately 1-2 weeks later shoots which develop on kanamycin-selected explants are excised with a sterile scalpel and planted in A medium (1 bag MS salts (Gibco), 10 gm sucrose, and 8 gm agar per liter) containing 100 mg/L kanamycin. Shoots which root in kanamycin are transferred to soil and grown in a growth chamber as described above.

Plant RNA Isolation

To analyze for expression of the DNA transformed into plants via the leaf disk inoculation procedure, RNA is isolated from the plant and tested for the presence of specific RNA transcripts encoded by the transforming DNA. After potting in soil and when the plants have grown to approximately the 10 leaf stage 1 gm of leaf tissue is harvested from each plant and frozen in liquid nitrogen. The frozen leaf tissue is ground in a mortar and pestle and then digested in 4 ml of proteinase K solution (250 ug/ml proteinase K in 50 mM Tris-HCl pH 9.0, 10 mM EDTA, and 2% SDS) for 10 minutes at 50° C. The solution is then extracted 2 times with equal volumes of phenol: chloroform: isoamyl alcohol (25:24:1), and the nucleic acids are precipitated from the aqueous phase with 0.6 volumes of isopropanol in the presence of 0.3M sodium acetate. After an overnight incubation at −20° C. the nucleic acids are collected by centrifugation at 12,000 × g and the pelleted precipitate is resuspended in 1.5 ml H$_2$O. The RNA is differentially precipitated from the DNA by addition of 0.5 ml of 8M LiCl and incubation on ice for 2 hours. The precipitate is collected by centrifugation at 4° C. for 20 minutes at 12,000 × g, resuspended in H₂O and reprecipitated as above with the same concentration of LiCl. The RNA is then resuspended in H₂O and precipitated by addition of 1/10th volume of 3.0M sodium acetate pH 6.0 and 2.5 volumes ethanol and incubation at −20° C. for greater than 4 hours.

RNAse protection Analysis

An RNAse protection procedure [Zinn et al., Cell 34, 865–879 1983, Melton et al., Nucleic Acids Res. 12, 7035–7056 (1984)] is used to detect the Avena phytochrome message in the RNA isolated from the transformed plants. An 800 bP DNA fragment which overlaps the transcription start site of the chimeric phytochrome gene and continues downstream into the coding region of the phytochrome gene is cloned into PGEM 3 (Promega Biotec) in such an orientation that SP6 RNA polymerase will generate a transcript complementary to the Avena phytochrome message. After hybridization between the probe and RNA isolated from the transformed plants, a subsequent RNAse treatment will remove any nonhybridizing RNA and leave only hybridized double stranded RNA. The protected region can be detected by gel electrophoresis. The riboprobe is generated using SP6 RNA polymerase and a promega Biotec kit as specified by the manufacturer in the presence of a [$^{32}$P] UTP (>3000 Ci/mM). Fifty micrograms of total RNA from transformed and control plants (prepared as described above) are mixed with $1 \times 10^6$ cpm of riboprobe and hybridized in 30 ul of solution containing 40 mM PIPES (PH 6.4), 400 mM NaCl, and 80% formamide for 16 hours at 45.5° C. The resulting hybrids are digested for 30 minutes at 30° C. with RNAse by adding 350 ul of solution containing 300 mM NaCl, 10 mM Tris-HCl pH 7.5, 5 mM EDTA, 40 ug/ml RNAse A and 2 ug/ml RNAse Tl. After the incubation the RNAse is destroyed by adding SDS to the digestion to a final concentration of 0.5% and treating it with 50 ug proteinase K for 30 minutes at 37° C. The RNAse and proteinase K treated hybrids are then extracted with an equal volume of phenol:chloroform:IAA (25:24:1) and precipitated with 2.5 volumes of ethanol. The RNA samples are analyzed on a 4.5% acrylamide gel containing 8M urea.

PROTEIN ANALYSIS

The presence of Avena phytochrome expression in the transformed plants can also be assessed at the protein level by detecting the Avena protein with specific antibodies or by assaying for increases in total phytochrome spectral activity in the dark and in the light. Phytochrome protein levels were determined using an immunoblot procedure employing either monoclonal or polyclonal antiphytochrome antibodies [described in Shanklin et al., Proc. Natl. Acad Sci USA. 84, 359–363 (1987)]. Polyclonal antibodies were generated in rabbits against highly purified Avena phytochrome and then purified by use of an Affi-Gel 10 column containing immobilized Avena phytochrome. Proteins were extracted from frozen tissue by homogenizing at 4° C. for 30 seconds in a solution of 50% ethylene glycol,100 mM Tris-HCl (pH 8.3), 140 mM ammonium sulfate, 20 mM sodium metabisulfite, 10 mM EDTA, and freshly added 4 mM phenylmethlylsulfonyl flouride (Buffer A). The extract was made 0.1% (wt/vol) in polyethylenimine by addition of a 10% (wt/vol) solution (pH 7.8), stirred for 5 minutes and clarified at 50,000 × g for 20 minutes. The protein concentration of the supernatant was determined using Bradford protein assay reagent (Biorad) and volumes of each extract containing 35 ug of protein was mixed 1:1 (vol/vol) with a solution of 10% glycerol, 3% SDS, 0.25M Tris-HCl (PH 6.8), 0.2 mg/ml bromophenol blue, and 0.7M β-mercaptoethanol were boiled for 3 minutes and run on a 7% SDS polyacylamide gel. After SDS polyacrylamide gel electrophoresis the proteins were transferred to nitrocellulose (HAHY 304 FO, Millipore) electrophoretically. Immunoreactive phytochrome bands were visualized colorimetrically by using rabbit antiphytochrome immunoglobulins in conjunction with alkaline phosphatase-conjugated goat IgGs directed against rabbit immunoglobulins and the phosphatase substrates nitro blue tetrazolium and 5-bromo-4-chloro-3-indolyl phosphate.

Spectral analysis of phytochrome activity was performed using proteins extracted as described above for the immunoblot analysis except that after addition of polyethylenimine and clarification by centrifugation, the phytochrome was precipitated by adding ammonium sulfate to 250 mg/ml and collected by centrifuging at 50,000 × g as described above. The pellet was resuspended in ½ strength buffer A (given above) which contained 14 mM β-mercaptoethanol instead of the sodium metabisulfite. Spectral quantitation of phytochrome was performed in this buffer using dual wavelength $A_{730}/A_{666}$ spectroscopy following saturating red or far-red irradiations, using a Shimadzu Uv3000 spectrophotometer. The extinction coefficient of $1.2 \times 10^5$ liter/mol/cm for Pr and a photoequilibrium of 86% Pfr in red light were used for all calculations of phytochrome content.

The present invention is further defined in the following EXAMPLES, in which all parts and percentages are by weight and degrees are Celsius, unless otherwise stated. It should be understood that these EXAMPLES, while indicating preferred embodiments of the invention, are given by way of illustration only. From the above discussion and these EXAMPLES, one skilled in the art can ascertain the essential characteristics of this invention, and without departing from the spirit and scope thereof, can make various changes and modifications of the invention to adapt it to various usages and conditions.

EXAMPLE 1

Construction of Plasmids pGP8.2-21, pGP8.2-22, pCV5, pCV5B and CV5B3 to Derive a DNA Construct Containing an Uninterrupted Phytochrome Coding Region Plasmids pAP3.1, pGP2.4-1, pGPB.2-1 and pGP8.2-2 were disclosed in Hershey et al., Nucl. Acids Res., 13:8543-8559 (1985)] and Hershey et al., [Gene 61:339-348 (1987)], and have been deposited on May 27, 1988 in the American Type Culture Collection (ATCC), Rockville, Md. 20852-1776. plasmid pAP3.1 bears the ATCC accession number 67713, pGP2.4-1 bears the ATCC accession number 67715, pGP8.2-1 bears the ATCC accession number 67714, and pGP8.2-2 bears the ATCC accession number 67716. Sequences from oat phytochrome genomic clones pGP8.2-1, pGP8.2-2, and pGP2.4-1, and cDNA clone pAP3.1 were used to create a chimeric gene which contains 1 kbp of 5′ promoter sequence from the type 3 phytochrome gene, a 5' untranslated leader, an uninterrupted coding region consisting of both types 3 and 4 phytochrome coding sequence and 1 kbp of 3' flanking sequence from the type 4 Avena phytochrome genes.

Figure 2:
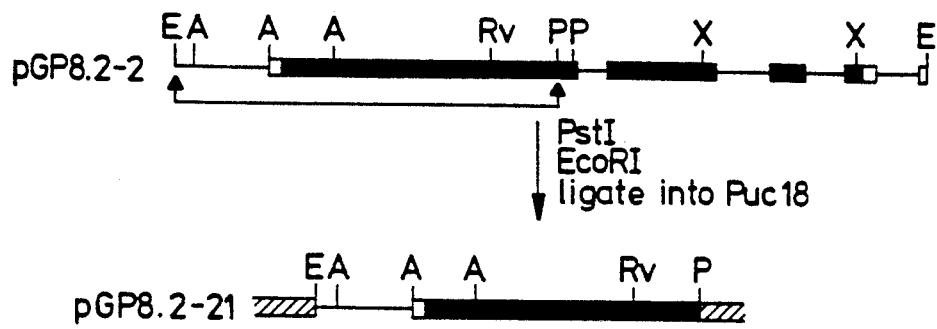
FIG. 2 is a physical map of pGP8.2-21 as derived from pGP8.2-2.

The 5' transcribed portion of the phytochrome type 3 gene was obtained by cleaving 2.5 ug pGP8.2-2 with Xba I, Eco RI, and Pst I in high salt buffer. Xba I cleaves a portion of the pGP8.2-2 plasmid which was not being cloned and was used in the digestion to reduce the number of clones containing undesirable inserts. The digestion results in the 5' transcribed region being present on a 2.56 kb fragment. The digestion products of pGP8.2-2 were mixed 1:1 (w:w) with the vector pUC18 which had been digested to completion with Eco RI and Pst I. After treatment with ligase overnight the mixture was used to transform E. coli JM107 and transformed bacteria were plated on LB agar plates containing 5 dibromo4chloro-3 indolyl-1-galactoside (X-gal) and isopropyl thiogalactoside (IPTG). Plasmid DNA was prepared from white colonies using a small scale plasmid DNA isolation procedure. This was accomplished by inoculating 5 ml aliquots of LB medium containing the appropriate antibiotic (ampicillin) with single bacterial colonies. After overnight incubation at 37° C. with vigorous shaking, 1.5 ml of each culture was poured into a microcentrifuge tube. The tubes were centrifuged for 20 seconds in a microcentrifuge and the media was removed by aspiration, leaving the bacterial pellets as dry as possible. An additional 1.5 ml of culture was added to the tubes and the above steps were repeated. The pellets were resuspended in 100 μl of an ice-cold solution of GTE buffer (50 mM glucose, 10 mM EDTA, 25 mM TRIS-HCl, pH 8.0) with 5 mg/ml lysozyme (added to the solution just before use) with vortexing. After 5 minutes at room temperature, 200 μl of a freshly prepared solution of lysis buffer (0.2N NaOH and 1% SDS) was added the contents were mixed by inverting rapidly two or three times. The tubes were placed on ice for 5 minutes, followed by addition of 150 μl of an ice-cold solution of potassium acetate pH 4.8 (made by adding 11.5 ml of glacial acetic acid and 28.5 ml of H2O to 60 ml of 5M potassium acetate). The contents were mixed by inverting the tubes sharply several times. After 5 minutes on ice, the tubes were centrifuged for 5 minutes in a microcentrifuge at 4° C. The supernatants were transferred to fresh tubes and an equal volume of phenol/chloroform was added to each with mixing. The resulting emulsions were centrifuged for 2 minutes in a microcentrifuge and the supernatants were transferred to fresh tubes. Two volumes of ethanol were added and the contents of the tubes were mixed well. After 2 minutes at room temperature, DNA was collected by centrifugation for 5 minutes at ambient temperature in a microcentrifuge. The supernatants were discarded and the tubes were stood in an inverted position on a paper towel to allow all of the fluid to drain away. The pellets were washed with 250 μl of 70% ethanol and the tubes were then recentrifuged. The supernatants were discarded and the pellets were dried briefly in a vacuum dessicator. Crude plasmid DNAs were dissolved in 50 μl of TE pH 8.0 and analyzed by appropriate restriction digestions until a plasmid was identified that contained the desired insert. This plasmid was designated pGP8.2-21 (see FIG. 2).

Figure 3:
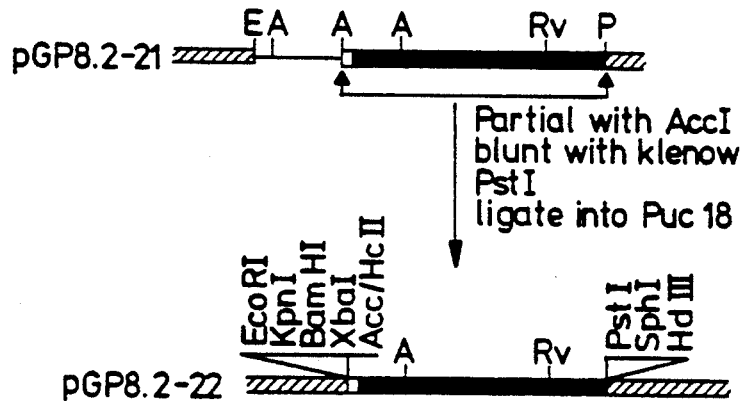
FIG. 3 is a physical map of pGP8.2-22 as derived from pGP8.2-21.

Ten micrograms of pGP8.2-21 were partially digested with the restriction endonuclease Acc I, using 0.8 units of enzyme per ug of DNA for 5, 10,15, and 20 minutes at 37° C. Under these digestion conditions all time points contained partially digested DNA, so the DNA from all time points were combined for subsequent processing. The 5' overhang of the Acc I sites were filled-in by adding one-tenth volume of 10X Klenow salts (0.5M Tris-HCl pH 7.2 or pH 7.5, 0.1M MgSO4, 10 mM DTT), one twentieth volume of a 5 mM deoxynucleotide triphosphate mix (all four dNTPs) and 1 unit of Klenow fragment of DNA polymerase I per μg of DNA. The fill-in reaction was incubated at room temperature for 30 mintues. The resulting blunt-ended DNA was cleaved with Pst I and ligated into the vector PUC18 that had been digested to completion with Pst I and Hind III. An aliquot of the ligation mixture was used to transform E. coli JM107, aliquots of the transformation mixture were plated on LB agar plus X-gal and IPTG, and individual plasmids from white colonies were analyzed until one was identified that contained the desired 1.9 kbp insert. The resulting plasmid, named pGP8.2-22, containing 1.9 kb of the phytochrome gene, including 38 bp of 5' untranslated sequence and 1.86 kb of protein coding sequence (see FIG. 3).

Figure 4:
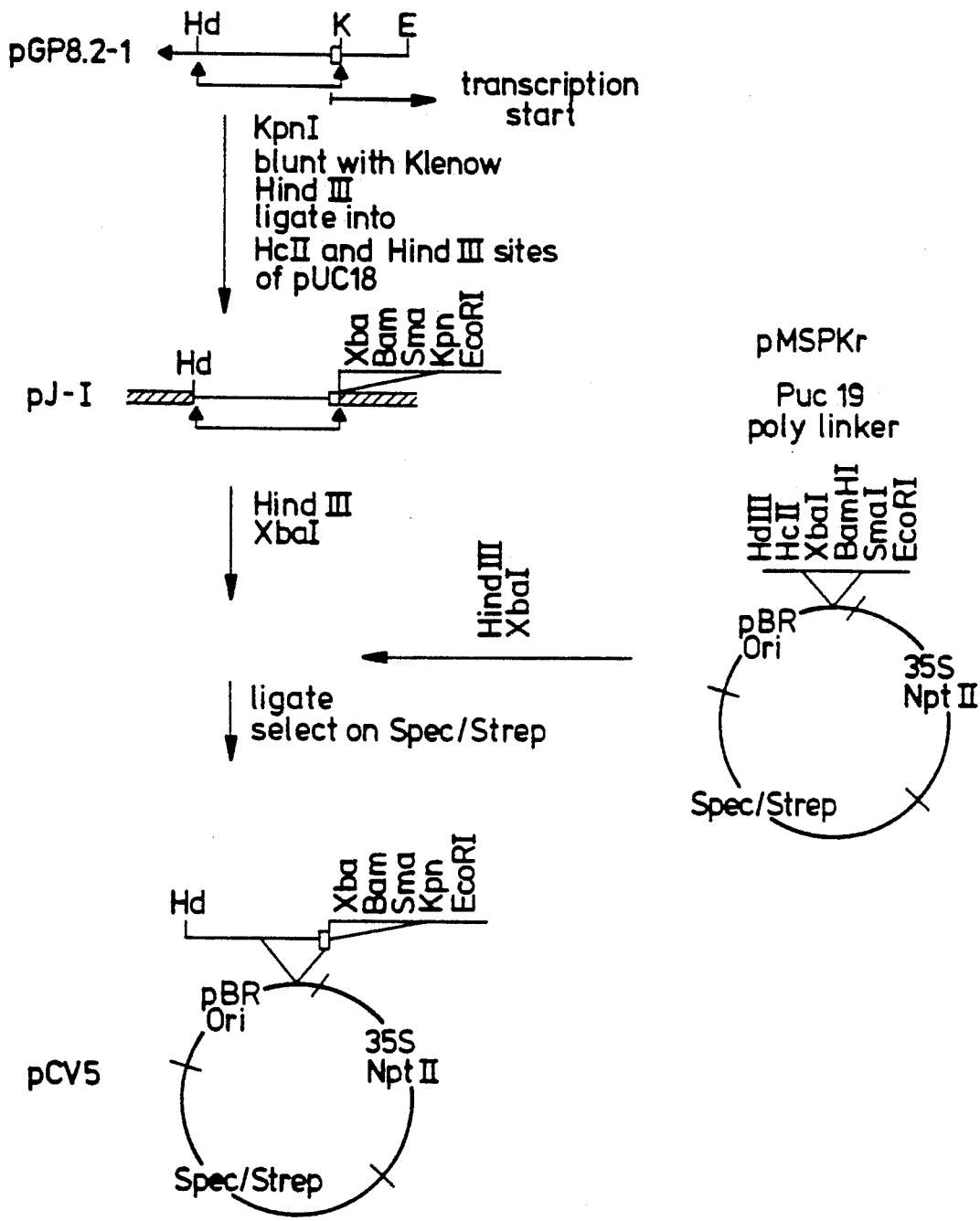
FIG. 4 is a physical map of pCV5 as derived from pGP8.2-1 and pMSPKr.

A region of the phytochrome type 3 gene containing the site of transcriptional initiation, the first 85 bp of the 5' untranslated leader sequence, and 1 kbp of upstream promoter sequence was obtained by digesting 10 ug of plasmid pGP8.2-1 to completion with Kpn I in low salt buffer. The 3' overhang of the Kpn I site was rendered blunt by incubation of the DNA with the Klenow fragment of DNA polymerase I for two hours using the reaction conditions described earlier in this Example. The polymerase was heat inactivated, and the blunt-ended DNA was digested to completion with Hind III. The resulting DNA was ligated in a 1:1 (w:w) ratio to pUC18 which had been cleaved with Hind II and Hind III. E. coli JM107 was transformed with an aliquot of the ligation and plated on LB agar containing X-gal and ITPG. White colonies were analyzed from the transformation plate, and a plasmid, called pJ-1, was obtained which contained the 1.1 kbp promoter from pGP8.2-1. The result of this cloning step was to add the restriction enzyme recognition sites from the pUC18 polylinker to the end of the 1.1 kbp fragment making many of these polylinker sites in pUC18 available for subsequent cloning steps. Plasmid PJ-I was cleaved with Xba I and Hind III and the 1.1 kbP promoter region was religated into the cloning vector pMSP'K (deposited in the American Culture Collection (ATCC), Rockville, Md., 10852 on Jun. 8, 1988, ATCC Deposit #67723) which had been digested to completion with Xba I and Hind III in high salt buffer. pMSP'K is a plasmid vector that contains the pUC19 polylinker, the pBR 322 origin of replication, a spectinomycin/streptomycin (spec/strep) resistance sequence, and the neomycin phosphotranferase II (NPT II) coding sequence bracketed by the upstream promoter region and downstream polyadenylation signal from the cauliflower mosaic virus 35S transcript as a selectable marker for plants (see FIG. 4). An aliquot of the ligation mixture was used to transform E. coli HB101 and individual spec/strep resistant colonies were analyzed until a plasmid was identified that contained the vector with the desired 1.1 kbp insert. This plasmid was designated pCV5. (see FIG. 4)

Figure 5:
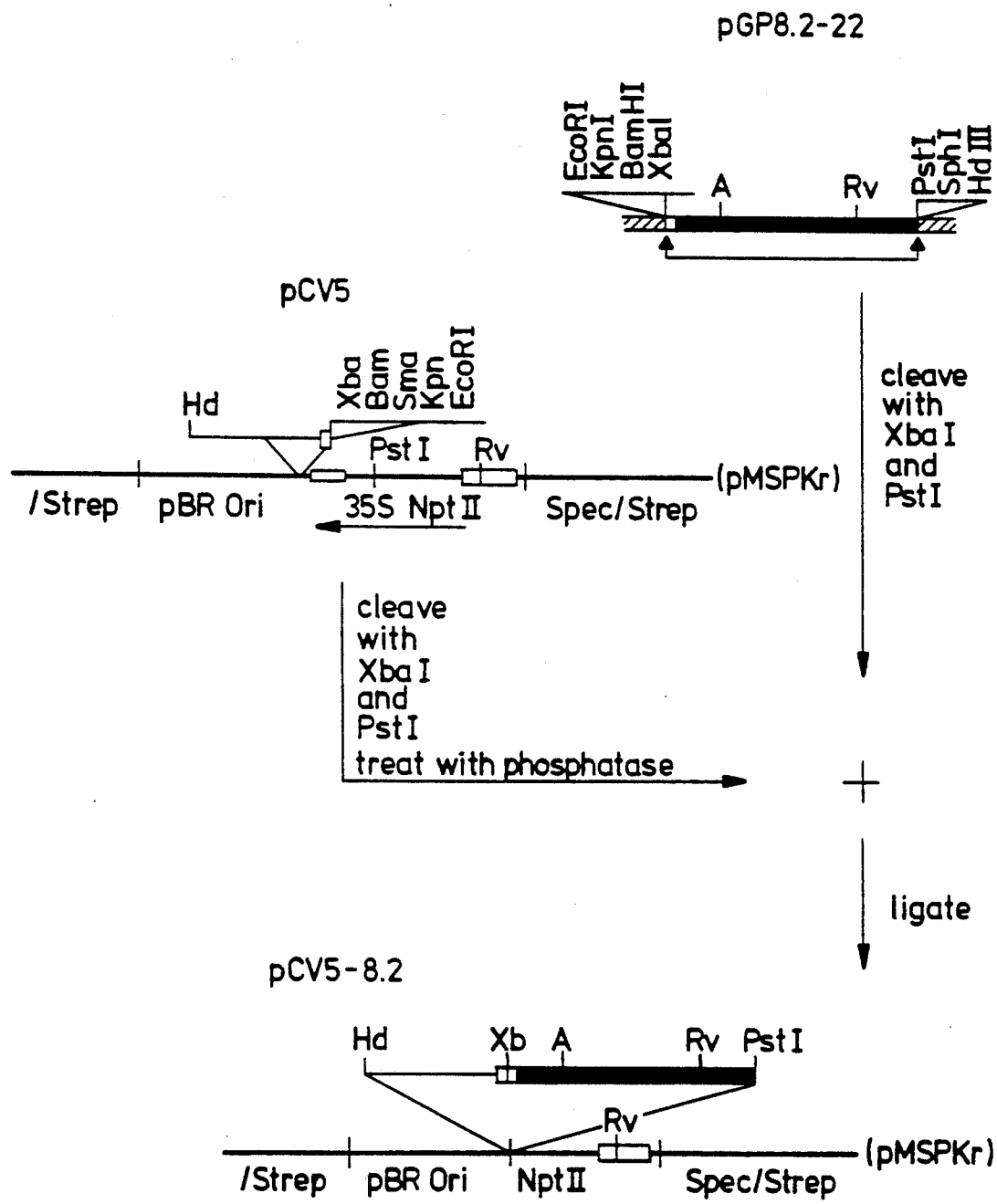
FIG. 5 is a physical map of pCV5-8.2 as derived from pCV5 and pGP8.2-22.
Figure 6:
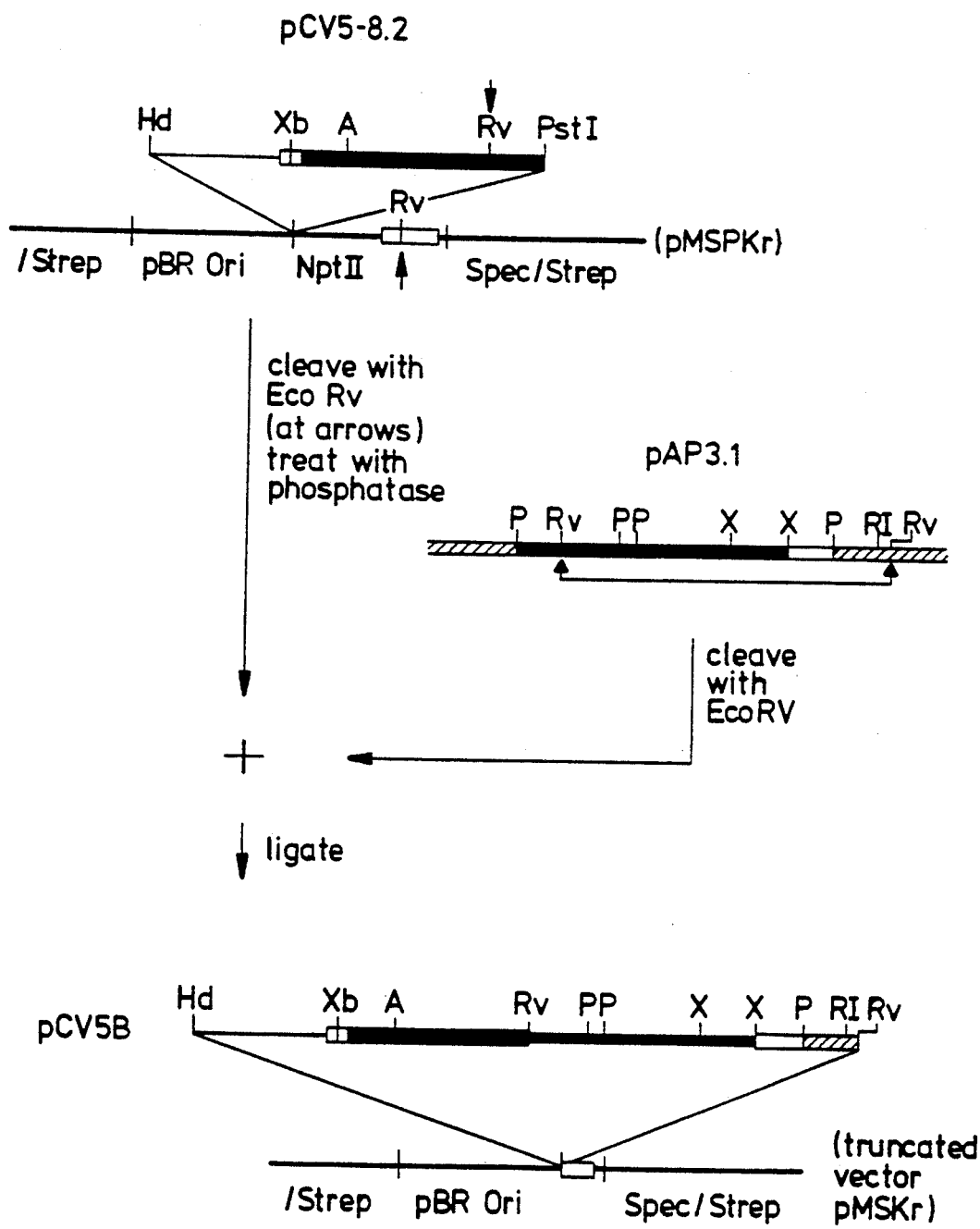
FIG. 6 is a physical map of pCV5B as derived from pCV5-8.2 and pAP3.1.
Figure 7:
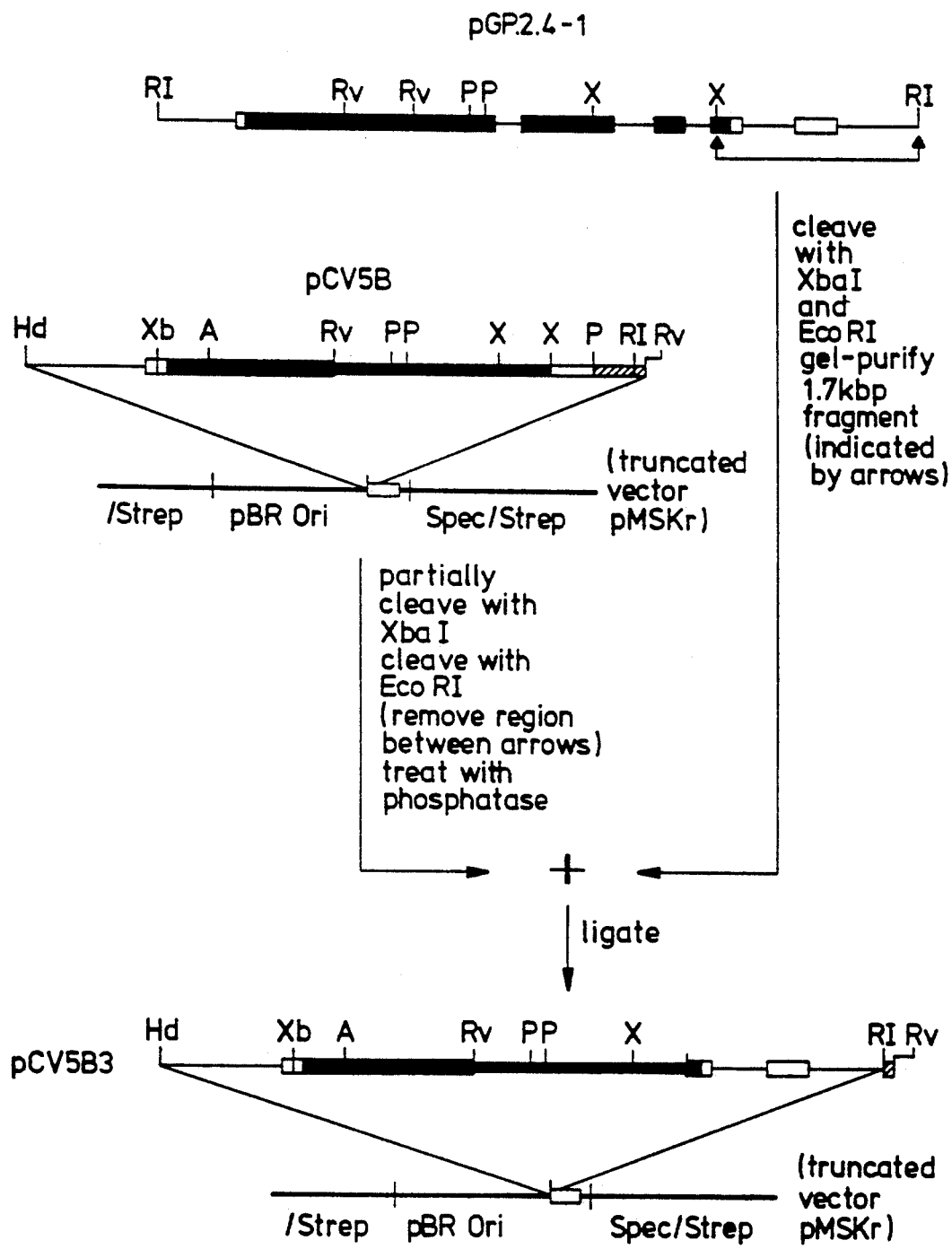
FIG. 7 is a physical map of pCV5B3 as derived from pGP2.4-1 and pCV5B.

The plasmids pCV5 (1.5 ug) and pGP8.2-22 (3 ug) were both digested to completion with Pst I and Xba I, and 1/10th of the DNA from each digestion was mixed in ligation buffer and ligated overnight at 16° C. An aliquot of the ligation mixture was used to transform E.

coli HB101 and individual spec/strep resistant colonies were analyzed until a plasmid was identified that contained the desired 1.9 kbp Pst I-Xba I fragment from pGP8.2-22 inserted into pCV5 (see FIG. 5). This plasmid was designated pCV5-8.2.

pCV5-8.2 and pAP3.1 (5 ug each) were digested to completion with the restriction enzymes Eco RV in high salt buffer. pCV5-8.2 was then dephosphorylated by making the restriction digest 0.1M in Tris-HCl pH 8.4 and incubating the DNA with 0.5 units of calf intestinal alkaline phosphatase (CIP) per microgram of DNA (Boehringer Mannheim Biochemicals) at 55° C. for 30 minutes. The phosphatase was inactivated by sequential extractions of the DNA solution with equal volumes of phenol (phenol as used is saturated with 0.1M Tris-HCl, pH 8.0 prior to use), phenol:chloroform (1:1) and chloroform. The DNA was precipitated by addition of sodium acetate to a final concentration of 0.3M followed by addition of two volumes of ethanol. After centrifugation and resuspension of Eco RV digested and dephosphorylated pCV5-8.2, 0.5 μg of both this DNA and the Eco RV digested pAP3.1 were mixed and ligated. An aliquot of the ligation mixture was used to transform E. coli HB101 and individual spec/strep resistant colonies were analyzed until a plasmid was identified that contained the desired 3.0 kbp Eco RV fragment from pAP3.1 (containing the bulk of the phytochrome protein coding region and a portion of pBR322 plasmid DNA) in pCV5-8.2. This plasmid was designated pCV5B (see FIG. 6).

pCV5B (5 ug) was partially digested with the restriction endonuclease Xba I in high salt buffer, using 20 units of enzyme per ug of DNA at 37° C. Aliquots were removed after 10, 15, 20, 25 and 30 minutes of digestion and stopped by adding 1 ul of 0.5M EDTA pH 8 to each aliquot. The 10, 15 and 20 minute time points had mostly linearized plasmid in them and so they were combined, and ethanol precipitated. The resulting DNA was digested to completion with Eco RI. Ten micrograms of plasmid pGP2.4-1 was digested to completion with Xba I and Eco RI, and run on a preparative 4.5% acrylamide gel. A 1.7 kbp band containing the sequence information for the C terminal coding region, promoter-distal intron, and 3' processing signals from the phytochrome type 4 gene was recovered from the gel by first staining it with ethidium bromide to visualize the DNA. A gel piece containing the desired 1.7 kbp fragment was cut out with a razor blade and crushed with a spatula. DNA was eluted from the gel fragment by suspending the crushed gel pieces in 400 μl of elution buffer (125 mM ammonium acetate, 1.5 mM magnesium acetate, 0.25 mM EDTA and 0.1% SDS) and shaking the resulting slurry overnight at 37° C. Gel fragments were removed from the slurry by filtration through glass wool and the DNA was recovered by ethanol precipitation. The eluted 1.7 kbp Eco RI- Xba I fragment was resuspended in 10 μl TE and 1 ul was ligated to 0.25 ug of the digested pCV5B DNA in a 20 ul ligation mixture. One microliter of the ligation mixture was used to transform E coli HB101. Individual spec/strep resistant colonies were analyzed until a plasmid was identified that contained the 1.7 kbp Xba I-Eco RI fragment of pGP2.4-1 inserted at the correct Xba I site in pCV5B see FIG. 7). The resulting plasmid was called pCV5B3 and contains a complete phytochrome coding region and 1 kbp each of 5' and 3' sequence from phytochrome genes.

EXAMPLE 2

Construction of the Plasmid pCV35phyt

Figure 8:
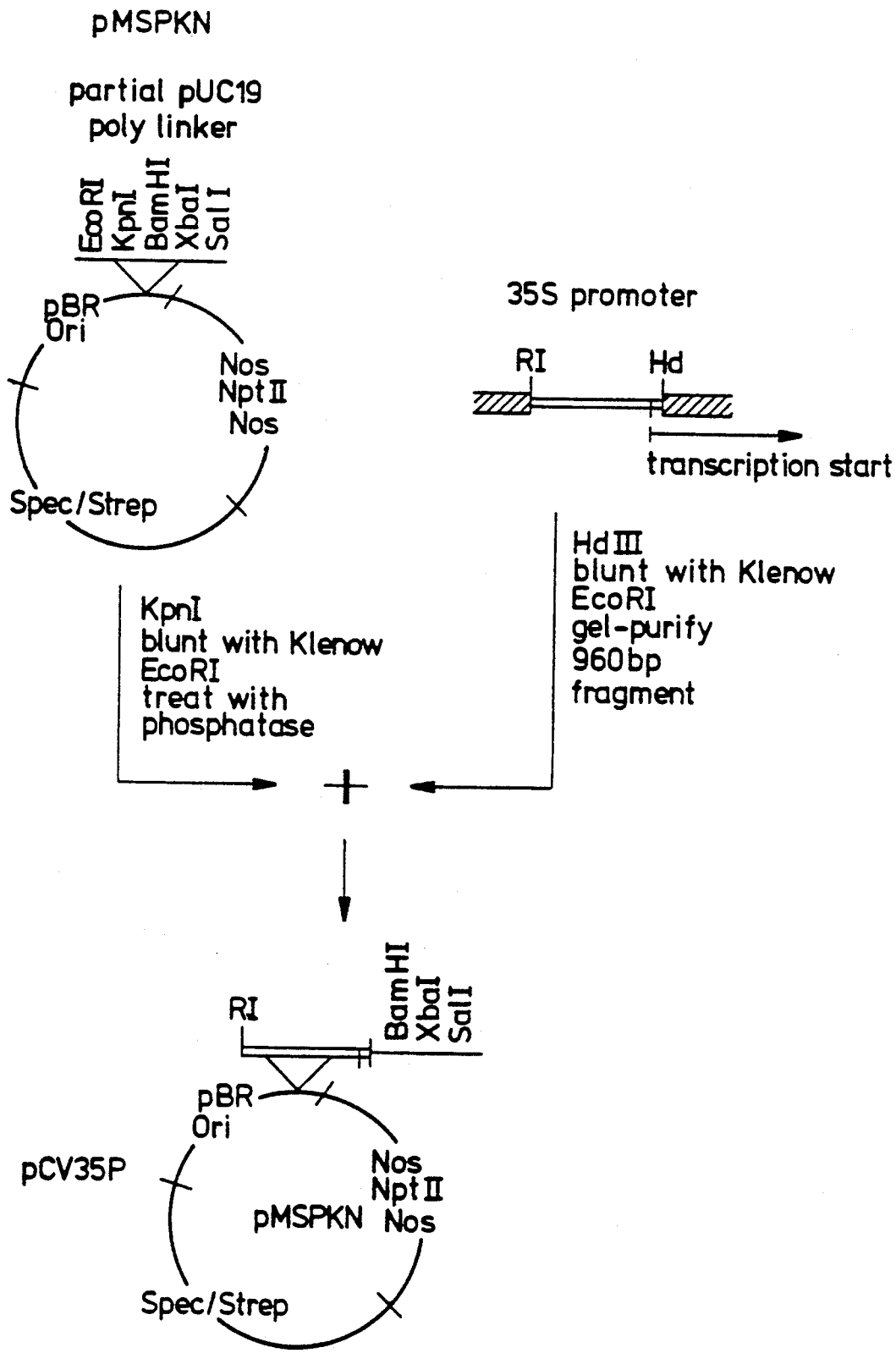
FIG. 8 is a physical map of pCV35P as derived from pMSPKN and pUC35K.
Figure 9:
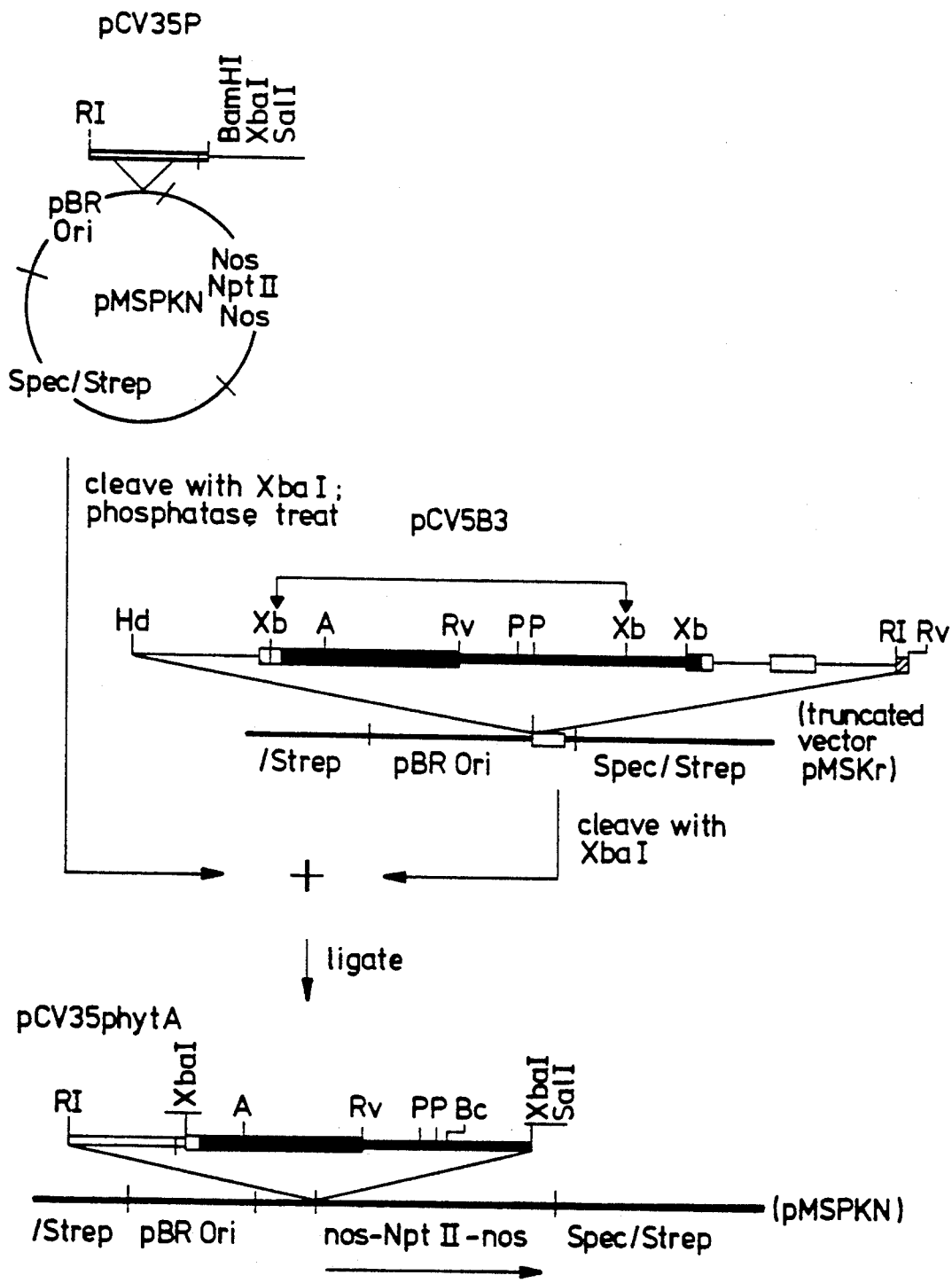
FIG. 9 is a physical map of pCV35phytA as derived from pCv35P and pCV5B3.

Plasmid pCV35phyt was constructed by removing the phytochrome promoter from the pCV5B3 plasmid and replacing it with DNA from the cauliflower mosaic virus (CaMV) between nucleotides 6493 and 7454. This sequence contains the promoter activity for the 35S transcript in CaMV [Odell et al., Nature 313: 810-812 (1985)] and is referred to as the 35S promoter. It is contained between Hind III and Eco RI restriction endonuclease sites in plasmid pUC35K (deposited Jan. 7, 1987 in the American Type Culture Collection (ATCC), Rockville, Md. 10852-1776, ATCC deposit #67285). Plasmid pUC35K (10 ug) was digested with Hind III to completion, the 5. overhanging ends were filled in with Klenow fragment as described in Example 1. The resulting blunt-ended fragment was digested to completion with Eco RI, run on a 4.5% acrylamide gel, and a 960 bp fragment containing the 35S promoter was purified. The 35S promoter was inserted into the cloning vector pMSPKN (deposited on Jun. 8, 1988 in the ATCC (Deposit #67722)) which to pMSPrK except that the 35S promoter and polyadenylation signals which are operably linked to the NPT II coding sequence in PMSPrK are replaced by the nopaline synthase promoter and polyadenylation signals in PMSPKN. pMSPKN was used to avoid any potential internal homologous recombination that might occur between the 35S promoter of the NPT II gene in pMSPrK and the 35S promoter linked to the phytochrome coding region. Any cloning vector containing suitable restriction sites for the cloning steps outlined below and either pBR322 sequences or sequences for autonomous replication in Agrobacterium tumefaciens can be used in place of PMSPKN. The cloning vector was prepared for insertion of the 35S promoter fragment by digesting 5 ug of it to completion with Kpn I. The resulting 3' overhang was made blunt as described for Kpn I sites in Example 1 and the resulting DNA was digested to completion with Eco RI (see FIG. 8), treated with phosphatase, and ligated to 1/10th volume of the gel-purified 35S fragment in a 20 ul ligation mixture containing 5% PEG. Individual plasmids were analyzed until one was identified that contained the 35S promoter in pMSPKN. The resulting construction is called pCV35P.

pCV5B3 (10 ug) and pCV35P (5 ug) were both cleaved to completion with Xba I in high salt buffer. pCV35P was then treated with phosphatase and 0.1 ug of the resulting DNA was mixed and ligated to 0.2 ug of the digested pCV5B3 DNA. One microliter of the ligation was used to transform E. coli HB101. Individual spec/strep resistant colonies were analyzed until a plasmid was found that contains the large (2.8 kbp) promoter proximal Xba I fragment from pCV5B3 in such an orientation that the 35S promoter would direct transcription of the phytochrome coding strand. The resulting plasmid is called pCV35phytA (see FIG. 9).

Figure 10:
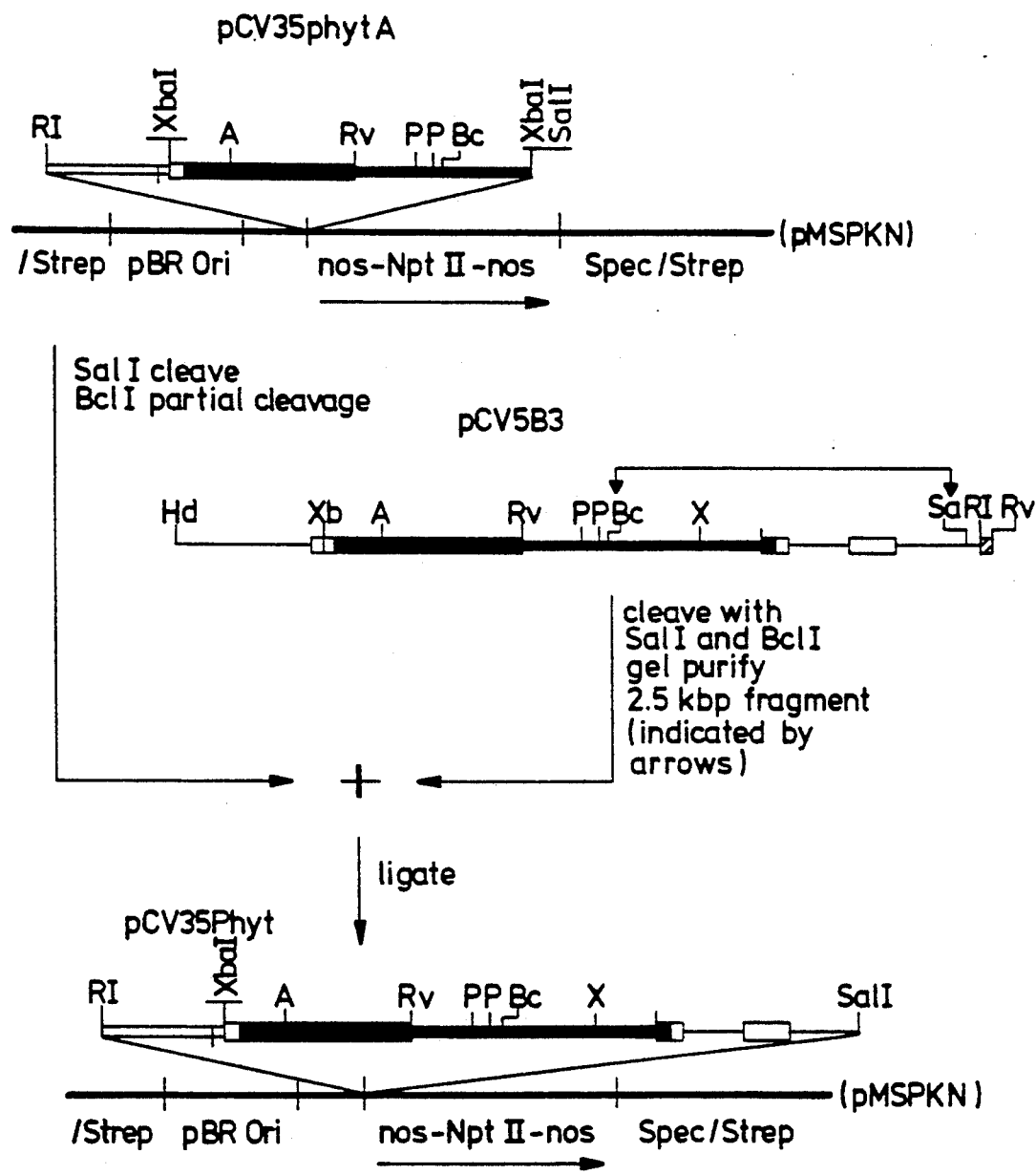
FIG. 10 is a physical map of pCV35phyt as derived from pCV35phytA and pCV5B3.

In order to obtain unmethylated DNA and create a Bcl I site within the phytochrome gene insert accessible for cleavage, the pCV35phytA plasmid was transformed into a dam⁻ E. coli strain. NS2626 was used in this work, but any commonly available dam⁻ strain of E. coli can be used to accomplish the invention. Competent dam⁻ cells were prepared by inoculating 50 ml of LB broth with 100 μl of an overnight culture of NS2626 and incubating the culture at 37° C. with shaking until the O.D.$_{650}$ reached 0.25. The cells were chilled to 0° C. on ice and bacteria were harvested by centrifugation at 1500 × g for 10 minutes, resuspended in 25 ml of 100 mM CaCl$_2$ and incubated on ice for 30 minutes. The bacteria were recentrifuged as above and resuspended in 1 ml of 100 mM CaCl$_2$ and placed on ice. After 4 hours on ice, 200 μl of competent cells were removed, transforming DNA was added, and the cells were incubated on ice for 30 minutes. The transformation mixture was heat shocked for 2 minutes in a 42° C. water bath without shaking The cells were returned to the ice for 2 minutes before addition of 1 ml of S.O.C. medium. The transformation then proceeded as described in Example 1. Twenty micrograms of unmethylated pCV35phytA was digested to completion with Sal I in high salt and then ethanol precipitated. The resulting plasmid DNA was partially digested with Bcl I because of a Bcl I site in the Spec/Strep$^r$ portion of the cloning vector. To do this, the pellet was resuspended in 100 ul and digested for 5 minutes with 18.2 units Bcl I at 37° C. using salt conditions specified by the supplier of the enzyme. pCV5B3 was also transformed into NS2626 and the unmethylated form of the plasmid was digested to completion with Bcl I and Sal I. The digested DNA was separated by electrophoresis in a 0.8% low melt agarose gel. After electrophoresis, the gel was stained with ethidium bromide and a piece of agarose containing the desired 2.5 kbp fragment was cut out and placed into a microfuge tube. The tube was then frozen at −80° C. for 30 minutes and thawed. The agarose was then crushed with a spatula and the tube was centrifuged in a microfuge for 10 minutes. The supernatant was removed from the tube without disturbing the agarose pellet at the bottom of the tube. The DNA was precipitated by adding 1/10 volume of 3M sodium acetate and 2 volumes of ethanol followed by a 15-30 minute incubation at −80° C. The DNA was recovered by centrifugation in a microcentrifuge for 15 minutes at 4° C. The DNA pellet was washed with 70% ethanol, dried under vacuum and resuspended in TE buffer. The resulting pCV5B3 DNA was ligated to the pCV35P DNA which had been digested partially with Bcl I and to completion with Sal I. An aliquot of the ligation mixture was used to transform E. coli HB101 and individual plasmids were analyzed until one was identified that had received the desired 2.5 kbp Bcl I/Sal I fragment containing the 3' end of the phytochrome gene from pCV5B3 inserted at the Bcl I site within the phytochrome coding sequence in pCV35P (see FIG. 10). The resulting plasmid was called pCv35Phyt and contains the complete phytochrome coding sequence from pCV5B3 operably linked to the 35S cauliflower mosaic virus promoter.

EXAMPLE 3

Overexpression of Phytochrome in Transgenic Tobacco pCV35phyt was mobilized from E. coli HB101 into Agrobacterium tumefaciens strain GV3850 via the triparental mating technique. E. coli strain HB101 containing the plasmid pRK2013 was used as a helper for plasmid mobilization in a triparental mating. Each strain of bacteria, HB101 containing the pCv35phyt construct, HB101 containing pRK2013, and Gv3850 was grown overnight in separate 5 ml Luria Bertain (LB) broth cultures in the presence of the appropriate selective antibiotic. The cells from the cultures were harvested by centrifugation at 4000 × g for 10 minutes at 22° C. and then resuspended in 5 ml LB broth. The mating was performed by mixing 100 μl of each of the three cultures in a 1.5 ml Eppendorf centrifuge tube and pipetting the entire mixture onto sterile nitrocellulose discs (Millipore HA type filters). Each nitrocellulose disk was placed on 6-8 sterile Whatman #1 filter paper disks to remove excess liquid from the culture and thereby concentrate the bacteria in the mixture. The nitrocellulose disks were then placed onto LB agar in a 100 mm petri dish and incubated for approximately 16 hours at 30° C. Following the incubation, the bacteria were washed from the nitrocellulose discs into a sterile 4 ml polypropylene culture tube using 1 ml of 10 mM MgSO$_4$. The bacteria were serially diluted and various dilutions were plated onto LB agar plates containing 100 μg/ml each of rifampacin, spectinomycin, and streptomycin. After a 3 day incubation at 30° C., resistant colonies growing on the plates were picked and the presence of the desired insert DNA was confirmed by Southern blot analysis of Ti plasmids prepared from individual colonies using the small scale plasmid isolation described in Example 1. A bacterial colony containing the pCV35Phyt construction in its Ti plasmid was identified and designated GV3850-35phyt.

The 35S promoter/phytochrome chimeric gene was mobilized into the plant genome via Agrobacterium tumifaciens infection of tobacco leaf disks using Gv3850-35phyt. Standard aseptic techniques for the manipulation of sterile media and axenic plant/bacterial cultures were followed, including the use of a laminar flow hood for all transfers. Potted tobacco plants for leaf disk infections were grown in a growth chamber maintained for a 12 hour, 24° C. day, 12 hour, 20° C. night cycle, with approximately 80% relative humidity, under mixed cool white flourescent and incandescent lights. Tobacco leaf disk infections were carried out essentially by the method of Horsch et al. (Horsch, R. B., Fry, J. E., Hoffman, N. L. Eichholtz, D., Rogers, S. G., and Fraley, R. T. (1985) Science., 227, 1229-1231).

Young leaves, not fully expanded and approximately 4-6 inches in length were harvested with a scalpel from approximately 4-6 week old tobacco plants. The leaves were surface sterilized for 30 minutes by submerging them in approximately 500 ml of a 10% Clorox, 0.1% SDS solution and then rinsing them 3 times with sterile deionized water. Leaf disks, 6 mm in diameter were prepared from whole leaves using a sterile paper punch.

Leaf disks were inoculated by submerging them for several minutes in 20 ml of a 1:10 dilution of an overnight LB broth culture of Agrobacteria carrying the pCv35phyt construction. After inoculation, the leaf disks were placed in petri dishes containing CN agar medium (1 bag MS salts (Gibco) 30 gm sucrose, 8 gm agar, 0.1 ml of 1 mg/ml napthalenacetic acid, and 1 ml of 1 mg/ml benzyl adenine per liter, pH 5.8). The plates were sealed with parafilm and incubated under mixed fluorescent and "Gro and Sho" plant lights (General Electric) for 2-3 days in a culture room maintained at approximately 25° C.

To rid the leaf disks of Agrobacteria and to select for the growth of transformed tobacco cells, the leaf disks were transferred to fresh CN medium containing 500 mg/L cefotaxime and 100 mg/L kanamycin. Cefotaxime was kept as a frozen 100 mg/ml stock and added aseptically (filter sterilized through a 0.45 μM filter) to the media after autoclaving. A fresh kanamycin stock (50 mg/ml) is made for each use and is filter sterilized into the autoclaved media.

Leaf disks were incubated under the growth conditions described above for 3 weeks and then transferred to fresh media of the same composition. Approximately 1-2 weeks later 53 shoots which develop from 80 kanamycin-selected leaf disks were excised with a sterile scalpel and planted in A medium (1 bag MS salts (Gibco), 10 gm sucrose, and 8 gm agar per liter) containing 100 mg/L kanamycin. Four shoots which rooted in kanamycin were transferred to soil and grown in a growth chamber as described above. These plantlets were designated 7A, 9A, 9B, and 54A and were potted in soil.

Individual transformed plants were analyzed for the presence of Avena phytochrome expression using an RNAse protection procedure. To accomplish this, a DNA fragment that overlaps the start of transcription in the Avena phytochrome type 3 gene was isolated from pCv5B3 (described in Example 1) by cleaving 10 ug of the plasmid with Hind III and Sal I in high salt buffer, running the digested DNA through a 4.5% polyacrylamide gel and purifying the desired 800 bp fragment. The DNA fragment was then ligated to pGEM 3 (Promega Biotec) which had been cut with Hind III and Sal I and treated with phosphatase. Individual plasmids were analyzed until one was identified that contained the Sal I-Hind III fragment from pCV5B3 in such an orientation that SP6 RNA polymerase would synthesize RNA complementary to the chimeric phytochrome message. The resulting pGEM plasmid was called pSP3.3 (shown as "probe" in FIG. 11). The plasmid pSP3.3 was linearized by cleavage with Eco RI and a [$^{32}$P] probe was generated from it using a Promega Biotec kit following the manufacturer's protocol.

To analyze for expression of the oat phytochrome in plants transformed via the leaf disk inoculation procedure, RNA was isolated from each kanamycin resistant plant and tested for the presence of a specific phytochrome RNA transcript encoded by the transforming DNA.

After the plants were potted in soil, and had grown to approximately the 10 leaf stage, 1 gm of leaf tissue was harvested from each plant and frozen in liquid nitrogen. The frozen leaf tissue was ground to a powder with a mortar and pestle and suspended in 4 ml of proteinase K solution (250 μg/ml proteinase K in 50 mM Tris-HCl pH 9.0, 10 mM EDTA, and 2% SDS) for 10 minutes at 50° C. The solution was then extracted 2 times with equal volumes of phenol:chloroform:isoamyl alcohol (25:24:1), and the nucleic acids were precipitated from the aqueous phase with 0.6 volumes of isopropanol in the presence of 0.3M sodium acetate. After an overnight incubation at −20° C. the nucleic acids were collected by centrifugation at 12,000 × g and the pellet was resuspended in 1.5 ml H$_2$O. The RNA was differently precipitated from the DNA by addition of 0.5 ml of 8 M LiCl and incubation on ice for 2 hours. The precipitate was collected by centrifugation at 4° C. for 20 minutes at 12,000 × g, resuspended in H$_2$O and reprecipitated as above with the same concentration of LiCl. The RNA was then resuspended in H$_2$O and precipitated by addition of 1/10th volume of 3.0M sodium acetate pH 6.0 and 2.5 volumes ethanol and incubation at −20° C. for greater than 4 hours. RNA was resuspended in H$_2$O and stored at −80° C.

An RNAse protection procedure (Zinn et al., Cell 34, 865-879 1983, Melton et al., Nucleic Acids Res. 12, 7035-7056, 1984) was then used to detect the Avena phytochrome message in the RNA isolated from the transformed plants. Fifty μg of RNA from each transformant were hybridized with 1×10$^6$ cpm of riboprobe generated from the pSP3.3 plasmid in 30 μl of solution containing 40 mM PIPES (pH 6.4), 400 mM NaCl, and 80% formamide for 16 hours at 45.5° C. The resulting hybrids were digested for 30 minutes at 30° C. with RNAse by adding 350 μl of solution containing 300 mM NaCl, 10 mM Tris-HCl pH 7.5, 5 mM EDTA, 40 μg/ml RNAse A and 2 μg/ml RNAse Tl. After the incubation, the RNAse was destroyed by making the digestion mixture 0.5% in SDS and treating it with 50 μg proteinase K for 30 minutes at 37° C. The RNAse and proteinase K treated hybrids were then extracted with an equal volume of phenol:chloroform:isoamyl alcohol (25:24:1) ard precipitated with 2.5 volumes of ethanol. The RNA samples were analyzed on a 4 5% acrylamide gel containing 8M urea. A fragment of 645 bP extending from the Xba I site at the phytochrome - 35S sequence junction in pCV35SPhyt to the first Hind III site internal to the phytochrome sequence (see FIG. 11) is expected to be protected by the probe in plants expressing the 35Sphyt construction.

Figure 11:
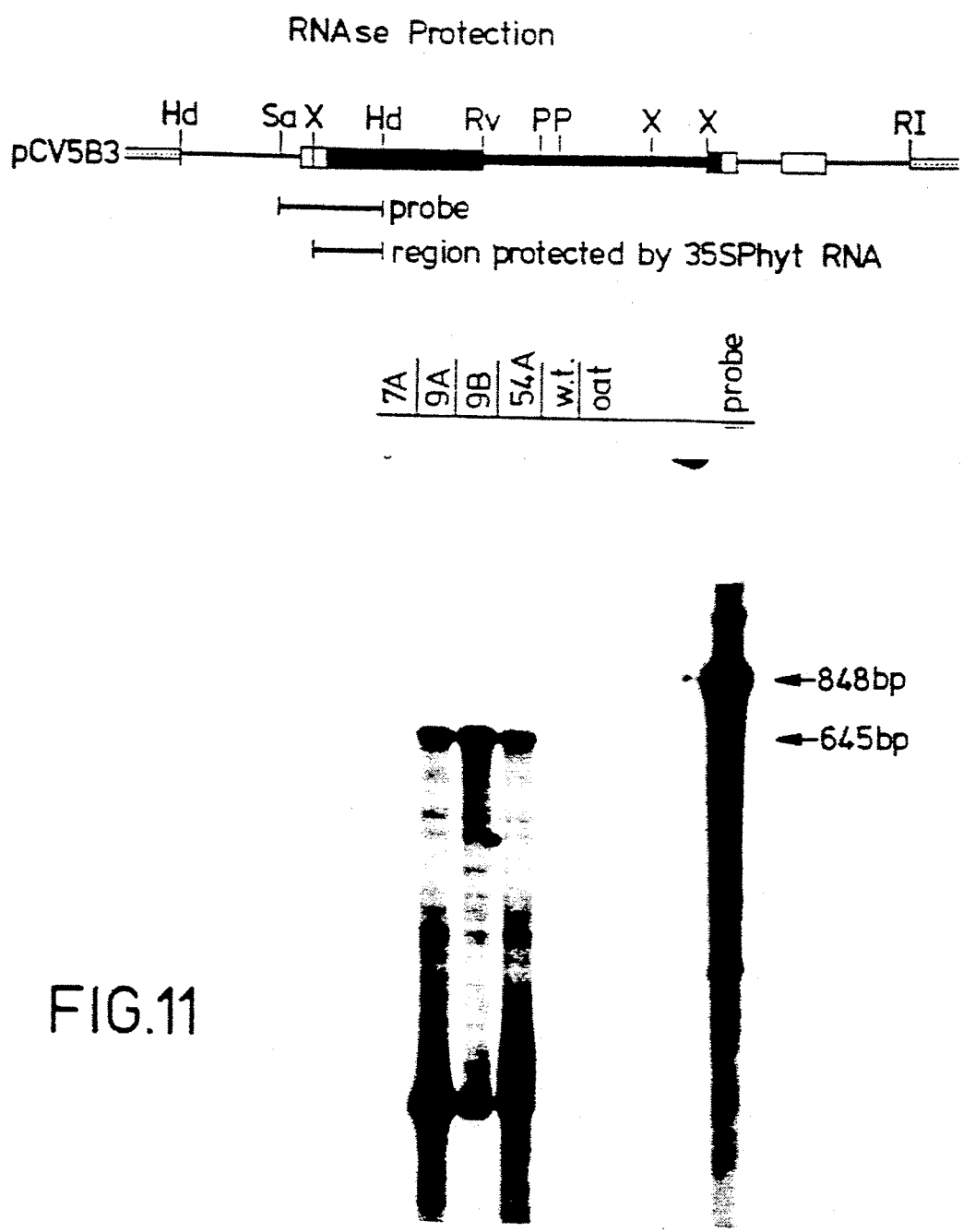
FIG. 11 is an autoradiograph showing protected Avena-type photochrome RNA in transformed tobacco plants.

The results of one such analysis are shown in FIG. 11. Ten micrograms of total RNA isolated from etiolated Avena seedlings 2 hours after red light irradiation was run in the experiment as a positive control for the expression of an Avena type phytochrome. Wild type tobacco RNA and RNA isolated from plant 7A showed no hybridization to the pSP3.3 probe under the experimental conditions described. However, RNA from plants 9A, 9B, and 54A showed strong hybridization signals yielding the predicted 645 base protected fragment. This result demonstrates that plants 9A, 9B, and 54A are producing high levels of stable Avena type phytochrome RNA even in the light when phytochrome levels would normally be extremely low.

Figure 12:
FIG. 12 is a color photograph showing the transformed plants 7A and 9A.

The tobacco plants transformed with the 35S phytochrome construction were allowed to grow to maturity. At this time it was observed that plants 9A, 9B, and 54A, which were shown to be overexpressing phytochrome by the RNAse protection analysis, were morphologically different from wild type tobacco (see FIG. 12). Plant 7A which was not overexpressing phytochrome, however, was morphologically indistinguishable from wild type tobacco. When compared to wild type plants, the three plants which were overexpressing phytochrome all showed increased green pigmentation, increased tillering (more stems formed from the base of the plant), reduced apical dominance, and reduced internodal distance. The latter trait resulted in plants which had the same number of leaf nodes to inflorescence but which were approximately half the height of normal plants. Plants 9A, 9B, and 54A had slightly smaller leaves than the nonexpressing plant, 7A, but flowered at approximately the same time and had comparable seed yield per inflorescense.

Tissue was harvested from the original transformed plants and/or from seedlings grown from seeds generated by self-fertilization of the transformed plants. The presence of Avena phytochrome expression in the tissues of these plants was assessed at the protein level by detecting the Avena protein with specific antibodies or by assaying for increases in total phytochrome spectral activity in the dark and in the light. Phytochrome protein levels were determined using an immunoblot procedure employing either monoclonal or polyclonal antiphytochrome antibodies (described in Shanklin et al., Proc. Natl. Acad. Sci. USA. 84, 359-363, 1987). Polyclonal antibodies were generated in rabbits against highly purified Avena phytochrome and then purified by use of an Affi-Gel 10 column containing immobilized Avena phytochrome. Proteins were extracted from frozen plant tissue by homogenizing at 4° C. for 30 seconds in a solution of 50% ethylene glycol, 100 mM Tris-HCl (pH 8.3), 140 mM ammonium sulfate, 20 mM sodium metabisulfite, 10 mM EDTA, and freshly added 4 mM phenylmethylsulfonyl flouride (Buffer A). The extract was made 0.1% (wt/vol) in polyethylenimine by addition of a 10% (wt/vol) solution (pH 7.8), stirred for 5 minutes and clarified at 50,000 × g for 20 minutes. The protein concentration of the supernatant was determined using Bradford protein assay reagent (Biorad) and equal volumes of each extract containing 35 μg of protein was mixed 1:1 (vol/vol) with a solution of 10% glycerol, 3% SDS, 0.25M Tris-HCl (ph 6.8), 0.2 mg/ml bromophenol blue, and 0.7M β-mercaptoethanol. The resulting samples were boiled for 3 minutes and proteins separated by SDS Polyacrylamide gel on a 7% gel. After electrophoresis, the proteins were transferred to nitrocellulose (HAHY 304 FO, Millipore) electrophoretically. Immunoreactive phytochrome bands were visualized colorimetrically by using rabbit antiphytochrome immunoglobulins in conjunction with alkaline phosphatase conjugated goat IgGs directed against rabbit immunoglobulins and the phosphatase substrates nitro blue tetrazolium and 5-bromo-4-chloro-3-indolyl phosphate.

Figure 13:
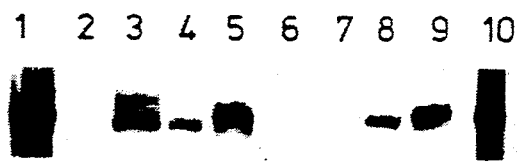
FIG. 13 is a protein immunoblot showing expression of the phytochrome polypeptide in the transformed plants grown under either light or dark growth conditions.

The results of one such analysis are shown in FIG. 13. The transformed plants 9A and 54A are clearly making full length phytochrome at much higher levels than wild type plants or plant 7A in both light grown and dark adapted shoots. Increased protein levels in plants 9A and 54A are due to the transforming Avena-like gene as indicated using monoclonal antibodies that recognize Avena but not the endogenous tobacco phytochrome. Full length Avena-type phytochrome is produced in second generation seedlings of 9A indicating that the gene is stably transmitted through the seed. Plant 9B was not tested in these experiments.

Phytochrome spectral activity in the transformed plants was measured on extracts of seedlings grown from seeds derived from self-fertilization of the 9A plant. Protein extracts were prepared as described above for the immunoblot analysis with the following modifications. After addition of polyethylenimine and clarification by centrifugation, the crude phytochrome was precipitated by adding ammonium sulfate to 250 mg/ml and collected by centrifuging at 50,000 × g as described above. The pellet was resuspended in ½ strength buffer A (given above) which contained 14 mM β-mercaptoethanol instead of the sodium metabisulfite. Spectral quantitation of phytochrome was performed in this buffer by employing dual wavelength (A730/A666) spectroscopy using a Shimadzu UV3000 spectrophotometer following saturating red or far-red irradiations of phytochrome samples. The extinction coefficient of $1.2 \times 10^5$ liter/mol/cm for Pr and a photoequilibrium of 86% Pfr in red light were used for all calculations of phytochrome content.

The results of such analyses indicates that there is 50% more phytochrome activity in dark grown 9A seedlings as compared to wild type with both Avena-type and tobacco phytochromes being present. In light-grown plants, however, there is at least 10 time more phytochrome activity in 9A seedlings than in light-grown wild type plants on a per ug protein basis. In addition, all detectable phytochrome in these light-grown plants is produced from the chimeric gene based on monoclonal antibody analysis.

Seeds of the dark-grown 9A tobacco plants described above were deposited with the American Type Culture Collection (Rockville, Md. 20852 USA) on Oct. 25, 1990 and are designated ATCC Accession No. 40914.

EXAMPLE 4

Figure 14:
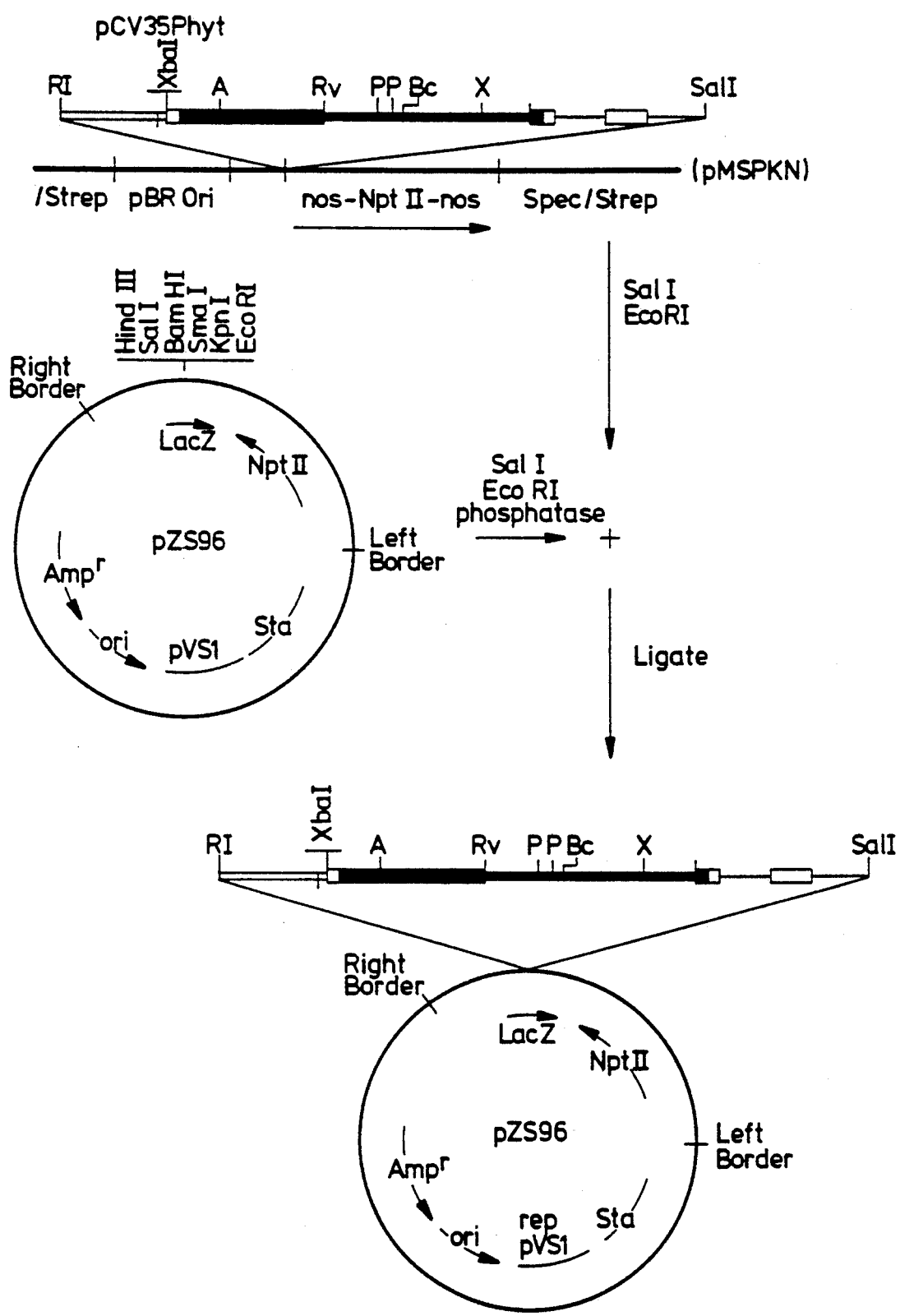
FIG. 14 is a physical map of pNPT35phyt as derived from pCV35Phyt and pZS96.

Plasmid PNPT35phyt was constructed by removing the entire 35S-phytochrome gene construction from pCV35phyt and recloning it into a binary vector. The binary vector pZS96 used to make pNPT35phyt is only one example of a large number of binary vectors that are available and may be used for this purpose. pZS96 contains a left border fragment from the octopine Ti plasmid pTiA6 and a right border fragment from pTiAch5 [van den Elzen, P., Lee, K. Y., Townsend, J., and Bedbrook J. Plant Molecular Biology, 5: 149-154, 1985]. The border fragments delimit the segment of DNA which becomes incorporated into the host plant genome during the process of Agrobacterium-mediated transformation. A chimeric marker gene (NOS/NPT II/OCS) which specifies kanamycin resistance in plant cells and the β-galactosidase (Lac Z) gene interupted by the polylinker sequence of pUC18 is positioned between the left and right border fragments. The ampicillin resistance gene and pBR322 origin of replication are contained outside of the T DNA border sequences for selection and amplification of the vector in E. coli. Sequences allowing stablization (sta) and replication rep) in Agrobacterium tumefaciens are also contained in pZS96 and were obtained from the plasmid, pVSl, of Pseudomonas aeruginosa [Itoh, Y., Watson, J. M., Haas, D., and Leisinger, T., Plasmid 11: 206-220, 1984].

pZS96 (10 μg) and pCv35phyt (10 μg) were cleaved to completion with Eco RI and Sal I in high salt buffer. pZS96 was then treated with alkline phosphatase as described in Example 1 and 0.1 μg of the resulting plasmid was ligated overnight with 0.2 μg of pCV35phyt. One microgram of the ligation was used to transform E. coli HB101 cells and plated on LB agar plates containing 50 g/ml ampicillin. Individual colonies were analyzed until a plasmid was identified which contained the 35S-phytochrome gene inserted into pZS96 (see FIG. 14).

pNPT35phyt was mobilized from E. coli HB101 to Agrobacterium strain LBA 4404 [Hoekema, A. Hirsch, P. R., Hooykass, P. J. J., and Schilperoort, R. A., Nature 303: 179-180, 1983] using the triparental mating procedure (see Example 3). LBA 4404 was grown in min A medium with sucrose (lX M9 salts [given in Maniatis, T. et al., (1982) Molecular Cloning, pg. 440], 1 mM MgSO4, 1 mM CaCl2, and 0.4% sucrose). LBA4404-NPT35phyt conjugates were selected on min A agar containing 100 μg/ml carbenicillin.

EXAMPLE 5

Overexpression of Phytochrome in Transgenic Tomato

Standard aseptic techniques for the manipulation of sterile media and axenic plant/bacterial cultures were followed, including the use of a laminar flow hood for all transfers.

Seeds of tomato (Lycopersicon esculentum var. Herbst Red Cherry) were surface sterilized for 30 minutes in a 10% Clorox, 0.1% SDS solution and rinsed 3 times with sterile deionized water. The seeds were planted in Magenta boxes (Magenta Corp.) containing 85 ml of OMS agar medium and germinated under mixed fluorescent and "Gro and Sho" plant lights (General Electric) in a culture room maintained at approximately 25° C. Cotyledons from 10-15 day old seedlings were used for the Agrobacterium inoculation.

Cotyledons were wounded by removing approximately 2 mm of tissue from each end of the cotyledon with a sterile scalpel. Wounded cotyledons were planted in petri dishes on CTM agar medium either with or without 75 mM acetosyringone (Aldrich Chemical).

In preparation for the cotyledon inoculation, a single colony of LBA4404-NPT35phyt (described in Example 4) from a Min A+tetracycline (1 µg/ml) agar plate was inoculated into a tube containing 3-5 ml of Min A broth and grown for 2 days at 28° C. in a New Brunswick platform shaker. On the morning of the cotyledon inoculation, the bacterial culture was diluted with sterile Min A broth to an $OD_{650}$ of 0.1 and allowed to multiply to an $OD_{650}$ of 0.3 under the growth conditions previously described. This culture was then used undiluted for the inoculation of cotyledon explants.

CTM agar plates containing the cotyledon explants were flooded with 5 ml of the LBA4404-NPT35phyt bacterial solution for approximately 5 mintues before removal of the solution. The plates were then secured with Time Tape (Shamrock Scientific Specialty) on two sides of the dish and incubated under mixed fluorescent and "Gro and Sho" plant lights (General Electric) at approximately 25° C. for two days.

To rid the plant cultures of excess Agrobacteria, the cotyledon explants were treated in OMS liquid media containing 500 mg/l cefotaxime for approximately 10 minutes. They were then transferred to fresh CTM medium containing 500 mg/l cefotaxime and 50 mg/l kanamycin and incubated under the same culture conditions described above for approximately 3 weeks. The cotyledons were then transferred to fresh media of the same composition and selective agents as CTM but with 1/10 the zeatin concentration.

After approximately 2-4 weeks, shoots developing from kanamycin-selected cotyledons were excised and planted in OMS media containing 500 mg/l cefotaxime and 0 or 50 mg/l kanamycin. Tomato shoots which had rooted after approximately 2-3 weeks have been transferred to soil in 8 inch pots and covered with plastic bags. The plants will be grown under mixed fluorescent and incandescent lights for a 12 hour, 24° C. day; 12, 20° C. night cycle, with approximately 80% RH, for one week before removing the plastic bags.

It is fully expected that as was the case with tobacco, the kanamycin resistant tomato plants regenerated will express the 35S-phytochrome construction and therefore overexpress a functional monocot phytochrome in the dark and in the light. These plants are expected to display the same phenotypic changes associated with phytochrome overexpression obtained in Example 3 with tobacco transformed with CV35phyt. These changes include reduce apical dominance, semidwarfism, increased shade tolerance, and a darker green color.

CTM Medium 1 pkg MS salts (Gibco)
1 ml B5 vitamins (per 100 ml: Nicotinic Acid 100 mg, thiamine, hydrochloride 1000 mg, pyridoxine hydrochloride 100 mg, M-inositol 10,000 mg)

3 mM MEs
3% glucose
0.7% agar
pH 5.7
Autoclave and add 1 ml 1 mg/ml zeatin stock OMS Medium 1 pkg MS salts (Gibco)
1 ml B5 vitamins (see above)
3 mM MEs
3% sucrose
0.8% agar
pH 5.7

| Min A + Tetracycline (1 µg/ml) Medium | |
|---|---|
| 1. Add 7.5 g agar to 400 ml $H_2O$ | |
| 2. Make stock: | |
| KPPO$_4$ | 5.25 g |
| KH$_2$PO$_4$ | 2.25 g |
| (NH4)$_2$SO$_4$ | 0.5 g |
| Sodium Citrate 2H$_2$O | 0.25 g |
| | 100 ml |
| 3. Make MgSO4 7H$_2$O stock = 20 g/100 ml, autoclaved | |
| 4. Make glucose stock = 20% solution, autoclaved | |
| 5. Make tetracycline stock = 1.0 mg/ml in ethanol/ H$_2$O, 50% v/v filter sterilized | |

Min A medium +1 ug/ml tetracycline

Mix (1) and (2)
Add 0.5 ml of (3), 5 ml of (4), and 0.5 ml of (5)

EXAMPLE 6

Overexpression of Phytochrome in Transgenic Brassica

Standard aseptic techniques for the manipulation of sterile media and axenic plant/bacterial cultures were followed, including the use of a laminar flow hood for all transfers.

Seeds of canola (Brassica napus var. Westar) were sterilized by stirring in a solution of 10% Chlorox, 0.1% SDS for 30 minutes. After rinsing thoroughly with sterile water, seeds were planted in glass crystallizing dishes containing germination medium (30 mM CaCl$_2$, 1.5% agar) using 75 seeds per dish. Dishes were then placed in the dark at 25° C. for five days.

An overnight culture of Agrobacterium strain LBA4404-NPT35phyt was begun by inoculating 3 ml of sterile liquid Min A medium with sucrose (see Example 4) containing 100 g/ml carbenicillin with a single colony. The culture was shaken at 28° C. for 18-20 hours with shaking.

Seeding hypocotyls were cut into 1 cm segments and placed immediately into plates containing 22.5 ml of bacterial dilution medium (MS liquid containing 100 µM acetosyringone). A 2.5 ml aliquot of the LBA4404-NPT35phyt overnight culture ($OD_{650}$=1.0 to 2.0) was added to each plate of bacterial dilution medium containing hypocotyl pieces. After 30 minutes, the hypocotyl pieces were removed from the bacterial suspension and placed into two cm grooves that were scored into the surface of fresh BC-1 plates containing 100 µM acetosyringone. The plates were dried briefly by leaving them open in a laminar flow hood for 30 minutes prior to their use. The dried surface of agarose was allowed to absorb excess liquid from the hypocotyl pieces and plates were then incubated for three days at 25° C. in dim light.

The explants were transferred from BC-1 plates to dishes containing explant washing solution (liquid MS containing 500 mg/L cefotaxime). Dishes were shaken slowly for three hours to wash Agrobacteria from the explants. The explants were then transferred to BC-1 plates containing 100 mg/l vancomycin, 50 mg/l kanamycin and placed in a 16:8 hour, light-dark chamber at 25° C.

After 21 days, the explants were transferred to fresh BC-1 plates containing 100 mg/l vancomycin, 50 mg/l kanamycin. Plates were then incubated for an additional 21 days in a growth chamber at 25° C. using a 16:8 light:dark cycle. When calli were at least 5 mm in diameter, they were transferred to BS-5 shoot induction medium containing 200 mg/l vancomycin and 25 mg/l kanamycin. Cultures were then maintained in continuous light at 25° C. during the induction period. Explants were transferred to fresh BS-5 every two weeks. Recognizable shoot primordia began to appear after three to ten weeks of growth on BS-5. Shoots were allowed to elongate somewhat prior to excision from the calli.

When first removed from BS-5, shoots were generally highly vitrified—thick, translucent, glassy leaf and stem tissue. They were subcultured for at least two three-week cycles on MSV-1A medium in order to normalize the plantlets. The shoot tip and several internodes below were transferred at each subculture and grown in a chamber using a short photoperiod—10 hour light/14 hours dark or 12 hour light/12 hour dark. This treatment also prevents flowering in culture.

Once shoots had normalized, they were planted directly into potting mix without attempting to root them in vitro. Shoots were excised near the agar surface and cut surfaces were dipped in Rootone (Security Lawn and Garden Products, Atlanta, Ga.). Shoots were planted in water-saturated Metro-Mix (W. R. Grace and Co.) in 8 inch pots and covered with plastic bags for two weeks until the plants were clearly growing.

RNA was extracted from the leaf tissue of a number of Brassica transformants and analyzed for the presence of Avena phytochrome expression using the RNA extraction and RNAse protection procedures described in Example 3. Wild type Brassica RNA showed no protection of the pSP3.3 probe under the experimental conditions described. However, RNA from all three transformed plants tested by RNAse protection showed strong hybridization signals, yielding the predicted 645 base protected fragment. This result demonstrates that these three plants are producing stable Avena phytochrome RNA, even in the light when phytochrome levels would normally be extremely low to undetectable.

It is fully expected that, as was the case with tobacco, the kanamycin resistant B. napus regenerants will express the Avena phytochrome protein and therefore overexpress a functional monocot phytochrome in the dark and in the light. As a consequence, these plants should display the same phenotypic changes associated with phytochrome overexpression obtained in Example 3 with tobacco transformed with CV35phyt as they mature. These changes include reduced apical dominance, semidwarfism, increased shade tolerance, and a darker green color.

| BRASSICA TISSUE CULTURE MEDIA | |
|---|---|
| Ingredient | Final Concentration |
| MS Major Salts | |
| $NH_4NO_3$ | 20.6 mM |
| $KNO_3$ | 18.8 mM |
| $MgSO_4-7H_2O$ | 1.5 mM |
| $KH_2PO_4$ | 1.25 mM |
| $CaCl_2-2H_2O$ | 3.0 mM |
| K3 Major Salts | |
| $KNO_3$ | 25.0 mM |
| $(NH_4)_2SO_4$ | 1.0 mM |
| $MgSO_4-7H_2O$ | 1.0 mM |
| $KH_2PO_4$ | 1.5 mM |
| $NH_4NO_3$ | 3.1 mM |
| $CaCl_2-2H_2O$ | |
| $CaCl_2-2H_2O$ | 6.3 mM |
| MS Micronutrients | |
| $MnCl_2-4H_2O$ | 100 uM |
| $H_3BO_3$ | 6200 uM |
| $ZnSO_4-7H_2O$ | 30 uM |
| KI | 830 uM |
| $NaMoO_4-2H_2O$ | 1.2 uM |
| $CuSO_4-5H_2O$ | 0.1 uM |
| $CoCl_2-6H_2O$ | 0.1 uM |
| Fe EDTA | |
| $Na_2$-EDTA | 100 uM |
| $FeSO_4-7H_2O$ | 100 um |
| I Vitamins | |
| Myo-Inositol | 100 mg/l |
| Thiamine | 0.5 mg/l |
| Glycine | 2.0 mg/l |
| Nicotinic acid | 5.0 mg/l |
| Pyrodoxine | 0.5 mg/l |
| Folic acid | 0.5 mg/l |
| Biotin | 0.05 mg/l |
| B5 Vitamins (1000X) | |
| Nicotinic Acid | 1 g/l |
| Thiamine Hydrochloride | 10 g/l |
| Pyridoxine Hydrochloride | 1 g/l |
| M-Inositol | 100 g/l |
| T Vitamins (10000X Stock Solution) | |
| Biotin | 50 mg/l |
| Pyridoxine Hydrochloride | 500 mg/l |
| Thiamine Hydrochloride | 500 mg/l |
| Nicotinic Acid | 5 g/l |
| Folic Acid | 500 mg/l |
| Glycine | 2 g/l |
| M-Inositol | 100 g/l |
| K3 Vitamins (10000X) | |
| Thiamine Hydrochloride | 1 g/l |
| Nicotinic Acid | 100 mg/l |
| M-Inositol | 100 g/l |
| T Vitamins | |
| Xylose | 200 mg/l |
| Sucrose | 10 g/l |
| MES | 0.6 g/l |
| DNA Grade Agarose | 2.5 g/l |
| pH 5.7 | |
| After autoclaving add: | |
| Zeatin | 2 mg/l |
| IAA | 0.1 mg/l |
| MSV-1A | |
| per liter: | |
| Sucrose | 10 g/l |
| T Vitamins | 1 X |
| DNA-Grade Agarose | 4 g/l |
| pH 5.8 | |
| MS Minimal Organic Medium | |
| MS Major Salts | |
| MS Micronutrients | |
| Myo-Inositol | 100 mg/l |
| Thiamine | 0.4 mg/l |
| BC-1 Medium | |
| MS Minimal Organic Medium | |
| Sucrose | 30 g/l |

-continued

| BRASSICA TISSUE CULTURE MEDIA | |
|---|---|
| Ingredient | Final Concentration |
| Mannitol | 18 g/l |
| 2,4-dichlorophenoxy acetic acid | 0.12 mg/l |
| Kinetin | 3 mg/l |
| DNA-Grade Agarose | 6 g/l |
| BS-5 Medium | |
| K3 Macronutrients | |
| MS Micronutrients | |
| $CaCl_2$—$2H_2O$ | 6.3 mM |
| $Na_2EDTA$ | 100 mM |
| $FeSO_4$—$7H_2O$ | 100 mM |

What is claimed is:

1. A transgenic, dicotyledonous plant which overexpresses phytochrome relative to the wild-type dicotyledonous plant in the dark and in the light.

2. A transgenic plant of claim 1 which is selected from the group consisting of alfalfa, soybean, petunia, cotton, sugarbeet, sunflower, carrot, celery, cabbage, cucumber, pepper, canola, tomato, potato, lentil, flax, broccoli, tobacco, bean, lettuce, oilseed rape, cauliflower, spinach, brussel sprout, artichoke, pea, okra, squash, kale, collard greens, tea and coffee.

3. A transgenic plant of claim 1 which is an ornamental plant selected from the group consisting of geranium, carnation, orchid, rose, impatiens, petunia, begonia, fuscia, marigold, chrysanthemum, gladiola, astromeria, salvia, veronica, daisey and iris.

4. Seed obtained by growing a transgenic plant of claim 1.

5. A recombinant DNA construct capable of transforming a plant comprising a single uninterrupted coding sequence for a phytochrome polypeptide operably linked upstream (5') to a nucleic acid promoter fragment and downstream (3') to a regulatory sequence containing a polyadenylation signal such that upon transformation said plant overexpresses phytochrome relative to the wild-type plant in the dark and in the light.

6. A recombinant DNA construct of claim 5 wherein the nucleic acid promoter fragment is derived from the genome of a virus.

7. A recombinant DNA construct of claim 6 wherein the nucleic acid promoter fragment is selected from the group consisting of the 35S and 19S constituents, of the cauliflower mosaic virus.

8. A recombinant DNA construct of claim 5 wherein the nucleic acid promoter fragment is derived from the opine synthase genes of Agrobacterium.

9. A recombinant DNA construct of claim 5 wherein the nucleic acid promoter fragment also contains an enhancer to further stimulate transcription and expression.

10. A recombinant DNA construct of claim 9 wherein the enhancer is derived from the genome of a virus.

11. A recombinant DNA construct of claim 10 wherein the enhancer is derived from the 35S promoter of the cauliflower mosaic virus.

12. A recombinant DNA construct of claim 9 wherein the enhancer is derived from the opine synthase genes of Agrobacterium.

13. A recombinant DNA construct of claim 5 wherein the single uninterrupted coding sequence for a phytochrome polypeptide is obtained by deletion of the introns from a coding sequence for a phytochrome polypeptide derived from a monocotyledonous plant.

14. A recombinant DNA construct of claim 13 wherein the coding sequence for a phytochrome polypeptide is derived from Avena.

15. A transgenic dicotyledonous plant containing a recombinant DNA construct of claim 5.

16. A transgenic dicotyledonous plant containing a recombinant DNA construct of claim 7.

17. Seed obtained by growing the transgenic plant of claim 15.

18. Seed obtained by growing the transgenic plant of claim 16.

19. A transgenic dicotyledonous plant of claim 1 which exhibits, relative to the wild-type plant, a phenotypic trait selected from the group consisting of reduced apical dominance, semidwarfism, increased shade tolerance, and dark green color.

* * * * *